United States Patent
Abraham et al.

(10) Patent No.: US 10,995,143 B2
(45) Date of Patent: May 4, 2021

(54) COMBINATION OF HUMAN ANTI-FGFR4 ANTIBODY AND SORAFENIB

(71) Applicants: Daiichi Sankyo Europe GmbH, Munich (DE); Daiichi Sankyo Company, Limited, Tokyo (JP)

(72) Inventors: Reimar Abraham, Munich (DE); Keisuke Fukuchi, Tokyo (JP)

(73) Assignees: Daiichi Sankyo Europe GmbH, Munich (DE); Daiichi Sankyo Company Limited, Tokyo (JP)

( * ) Notice: Subject to any disclaimer, the term of this patent is extended or adjusted under 35 U.S.C. 154(b) by 215 days.

(21) Appl. No.: 16/076,776

(22) PCT Filed: Feb. 9, 2017

(86) PCT No.: PCT/EP2017/052893
§ 371 (c)(1),
(2) Date: Aug. 9, 2018

(87) PCT Pub. No.: WO2017/137503
PCT Pub. Date: Aug. 17, 2017

(65) Prior Publication Data
US 2019/0048088 A1 Feb. 14, 2019

(30) Foreign Application Priority Data
Feb. 10, 2016 (EP) .................................. 16155056

(51) Int. Cl.
| | | |
|---|---|---|
| *C07K 16/28* | (2006.01) | |
| *A61K 39/395* | (2006.01) | |
| *A61K 31/44* | (2006.01) | |
| *A61P 35/00* | (2006.01) | |
| *A61K 31/4412* | (2006.01) | |
| *A61K 38/20* | (2006.01) | |
| *A61K 45/06* | (2006.01) | |
| *C07K 14/54* | (2006.01) | |
| *A61K 39/00* | (2006.01) | |

(52) U.S. Cl.
CPC .......... *C07K 16/2863* (2013.01); *A61K 31/44* (2013.01); *A61K 31/4412* (2013.01); *A61K 38/20* (2013.01); *A61K 39/3955* (2013.01); *A61K 39/39558* (2013.01); *A61K 45/06* (2013.01); *A61P 35/00* (2018.01); *C07K 14/54* (2013.01); *A61K 2039/505* (2013.01); *C07K 2317/21* (2013.01); *C07K 2317/33* (2013.01); *C07K 2317/34* (2013.01); *C07K 2317/565* (2013.01); *C07K 2317/76* (2013.01); *C07K 2319/30* (2013.01)

(58) Field of Classification Search
CPC .............. C07K 16/2863; C07K 14/54; C07K 2317/21; C07K 2317/33; C07K 2317/34; C07K 2317/565; C07K 2317/76; A61K 2039/505; A61K 31/4412; A61K 38/20; A61K 39/3955; A61K 45/06; A61P 35/00
See application file for complete search history.

(56) References Cited

U.S. PATENT DOCUMENTS

| | | |
|---|---|---|
| 10,358,498 B2 | 7/2019 | Abraham |
| 2007/0248604 A1 | 10/2007 | Desnoyers |
| 2011/0150903 A1 | 6/2011 | Baurin et al. |

FOREIGN PATENT DOCUMENTS

| | | |
|---|---|---|
| JP | 08208750 A | 8/1996 |
| WO | 201204654 A1 | 8/2012 |
| WO | 2016023894 A1 | 2/2016 |
| WO | 2014160160 A2 | 12/2019 |

OTHER PUBLICATIONS

Rudikoff et al., Single amino acid substitution altering antigen-binding specificity. Proc. Natl. Acad. Sci. USA 79:1979-1983, 1982.*
Harding, et al., "Predicting Responsiveness to Sorafenib: Can the Determination of FGF3/FGF4 Amplifications Enrich for Clinical Benefit" Hepatobiliary Surgery and Nutrition, vol. 3, No. 4, Aug. 2, 2014, pp. 168-171.
French, Dorothy M., Targeting FGFR4 inhibits Hepatocellular Carcinoma in Preclinical Mouse Models, PLoS ONE, www.piosone.org, May 2012, pp. 1-12, vol. 5, Issue 5.
Hoeflinch et al, "First Selective Small Molecule Inhibitor of FGFR4 for the Treatment of Hepatocellular Carcinomas with an Activated FGFR4 Signaling Pathway", Jrnl of Hepatology, vol. 62, 2015, pp. S215-S216.
Gao et al., "FGF19/FGFR4 Signaling Contributes to the Resistance of Hepatocellular Carcinoma to Sorafenib", Jrnl Experimental and Clinical Cancer Research, vol. 36, No. 1, Jan. 9, 2017, pp. 1-10.
Chen, Chaoyuan, Generation and Characterization of a Panel of Monoclonal Antibodies Specific for Human Fibroblast Growth Factor Receptor 4 (FGFR4), Hybridoma, 2005, pp. 152-159, vol. 24, No. 3, Mary Ann Liebert, Inc.
Elshorst, Bettina, 1H, 13C and 15N assignment of D2 domain of human fibroblast growth factor receptor 4, Biomol NMR Assign, 2013, pp. 179-182, vol. 7, Springer Science+Business Media B.V.
Mellor, Howard R., Targeted inhibition of the FGF19-FGFR4 pathway in hepatocellular carcinoma; translational safety considerations, Liver International, 2014, pp. e1-e9, ISSN 1478-3223, John Wiley & Sons Ltd.
PCT Application No. PCT/EP2016/061131 International Search Report and Written Opinion, dated Sep. 2, 2016.

(Continued)

*Primary Examiner* — Ruixiang Li
(74) *Attorney, Agent, or Firm* — Withers & Key, LLC

(57) ABSTRACT

The present invention relates to the medical use of antibodies against the FGF receptor 4 (FGFR4) combined with Sorafenib, in particular for the prevention or treatment of hyperproliferative diseases associated with FGFR expression, overexpression or hyperactivity.

8 Claims, 5 Drawing Sheets
Specification includes a Sequence Listing.

(56) References Cited

OTHER PUBLICATIONS

Hongfei Ge et al. "Fibroblast Growth Factor Receptor 4 (FGFR4) Deficiency improves Insulin Resistance and Glucose Metabolism under Diet-induced Obesity Conditions", Jrnl. Bio. Chem., vol. 289, No. 44, Oct. 2014, pp. 30470-30480.

Xing Xian Yu et al., peripheral Reduction of FGFR4 with Antisense Oligonucleotides Increases Metabolic Rate and Lowers Adiposity in Diet-Inducted Obese Mice; PLOS One, vol. 8, No. 7, Jul. 2013, pp. e66923.

2017-557187 Japanese Office Action, dated Dec. 23, 2019.

EP15/168152.5, Extended European Search Report, dated Oct. 16, 2015.

Neuberger et al., "Antibody Mediated Hepatocyte Injury in Methyl Dopa Induced Hepatotoxicity", Gut vol. 26, pp. 1233-1239, 1985.

Yamagiwa et al., "Presence of Antibodies Against Self Human Leukocyte Antigen Class II Molecules in Autoimmune Hepatitis", International Jrnl Medical Sciences, vol. 11, No. 9, pp. 850-856, 2014.

Waters et al., Managing Bile Acid Diarrhoea. Therap Adv Gastroenterol, Nov. 3, 2010 (6) pp. 349-357.

Brown, et al., "Tolerance to Single, but Not Multiple, Amino Acid Replacements in Antibody VH CDR2", American Associations of Immunologists, XP002649029, 1996, pp. 3285-3291.

Maynard, et al., "Protection Against Anthrax Toxin by Recombinant Antibody Fragments Correlates with Antigen Affinity", Nature Publishing Group, vol. 20, Jun. 2002. pp. 597-301.

Barderas et al., "Affinity Maturation of Antibodies Assisted by in Silico Modeling", PNAS, vol. 105, No. 26, Jul. 2008, pp. 9029-9034.

Winkler et al., "Changing the Antigen Binding Specificity by Single Point Mutations of an Anti-p24 (HIV-1) Antibody", American Association of Immunologists, Apr. 2010, pp. 4505-4514.

\* cited by examiner

COMBINATION OF HUMAN ANTI-FGFR4 ANTIBODY AND SORAFENIB

This application is being filed as the national stage patent application of PCT International Patent Application No. PCT/EP2017/052893, filed on 9 Feb. 2017, and claiming priority to European Patent Application Serial No. 16155056.1, filed on 10 Feb. 2016, and entitled "COMBINATION OF HUMAN ANTI-FGFR4 ANTIBODY AND SORAFENIB," the contents of both of which is incorporated herein by reference in its entirety.

The present invention relates to the medical use of antibodies against the FGF receptor 4 (FGFR4) combined with Sorafenib for the prevention or treatment of hyperproliferative diseases, in particular cancer.

Cancer chemotherapy has been one of the major medical advances in the last decades. However, conventional chemotherapy typically does not discriminate effectively between rapidly dividing normal cells and tumor cells, thus leading to several toxic side effects. In contrast, targeted therapies that have been introduced in recent years are directed against cancer-specific molecules and signaling pathways. Thus, targeted therapies have a high specificity toward tumor cells, providing a broader therapeutic window with less toxicity. Tyrosine kinases are an especially important target because they play an important role in the modulation of growth factor signaling.

Fibroblast growth factors (FGFs) are family of growth factors with diverse biological activities with members involved in angiogenesis, wound healing, embryonic development and various endocrine signaling pathways. The human FGF family comprises 18 members, which are structurally related signaling molecules. They exert their biological activity by interacting with their cognate receptors (FGFRs), a family of receptor tyrosine kinases. The mammalian FGFR family has four members: FGFR1-4 each consisting of three extracellular immunoglobulin-type domains (D1-D3), a single-span transmembrane domain and an intracelluar split tyrosine kinase domain. FGFs interact mostly with the 2 and 3 domains. Each FGFR binds to a specific subset of the FGFs. Most FGFs can bind to several different FGFR subtypes whereas others activate specifically one receptor or one isoform of a receptor.

The receptor-ligand interactions result in receptor dimerization and autophosphorylation, formation of complexes with membrane-associated and cytosolic accessory proteins, and initiation of multiple signaling cascades. The FGFR-FGF signaling system plays important roles in the development and tissue repair by regulating cellular functions and processes such as growth, differentiation, migration, morphogenesis and angiogenesis.

FGFR4 signaling is activated by several FGFs that activate also other members of the FGFR family (Omitz et al., 1996, *J. Biol. Chem.*, 1996, 271: 15292-7) while FGF19 is specific for FGFR4 (Xie et al., 1999, *Cytokine*, 11(10):720-35). The activation of the FGFR4 receptor results in several types of cell signaling including the setting-up of a phosphorylation cascade-mediated signaling pathway subsequent to stimulation of FGFR4 by FGF. Upon binding of the ligand to the extracellular domain of FGFR4, receptor dimerization and subsequent phosphorylation of tyrosine kinase residues results in activation of signaling pathways by inducing the binding of signaling molecules to the receptor (Vainikka et al., 1992, *EMBO*, 11(12):4273-4280, and 1994, *J. Biol. Chem.* 269:18320-18326). For example, FGFR4 associates with PLCγ1 and an increase in MAP kinase activation and DNA synthesis upon a FGF simulation has been observed. Further interaction with other human FGF growth factor receptor family members may expand the signaling potential of FGFR4 and is a means not only for signal diversification but also signal amplification (McKeehan W. L. and Kan M, 1994, *Mol. Reprod. Dev.* 39:69-82). An 85 kDa serine kinase has been found to negatively regulate tyrosine phosphorylation of FGFR4, but its exact function has not been elucidated (Vainikka et al 1996, *J. Biol. Chem.* 271:1270-1273). Association of FGFR4 with NCAM has been demonstrated to mediate integrin-dependent adhesion (Cavallaro et al., 2001. Nat. Cell Biol. 3:650-657), which might play a decisive role in tumor metastasis.

FGFR4 has been reported to have several cellular roles. The receptor is involved in the control of various cell differentiation processes in vitro and in vivo such as skeleton muscle differentiation and regeneration, mesenchymal differentiation, or osteogenesis or else in the formation of alveoli during postnatal hepatic development. Further, FGFR4 is described in the control of bile acid and cholesterol homeostasis and is thought to be involved in the control of adiposity. Furthermore, the balance between bile production and cholesterol production is controlled by FGFR4 in vitro and in vivo. FGFR4 is also involved in certain tumor phenomena such as the development of hepatocellular carcinomas or colon cancers, or in the proliferation of mammary fibroadenoma cells or of mammary cancer epithelial cells such as mammary or colorectal carcinoma cell motility. The overexpression of FGFR4 is also described in certain pancreatic cancer lines and correlates with astrocytoma malignancy.

The involvement of FGFR4 in various disorders makes the receptor an interesting target for diagnostic and therapeutic applications. In this context, an effective strategy is the usage of antibodies against FGFR4. In particular, antibodies that interfere with FGFR4-mediated signaling are desirable. Examples of FGFR4 antibodies are described in the literature such as in international applications WO 03/063893, WO 2012/138975, WO 2013/0183319 and in US application US 2011/010,903. Bumbaca et al. (mAbs 3:4, 1-11; 2011) describes a humanized anti-FGFR4 antibody that binds with high specificity to G receptor 4.

Recently, it was found that antibodies directed against an epitope between amino acids 119-284 of human FGFR4 or functional fragments thereof are particularly useful for therapeutic and diagnostic applications. These antibodies are described in international application PCT/EP2015/068440; the disclosure of which is incorporated herein by reference. The described human antibodies were found to be particularly useful for therapeutic and diagnostic applications. They specifically bind to FGFR4 and preferably show no cross-reactivity to other FGF receptors FGFR1-3b, c. Further, the antibodies are capable of inhibiting ligand binding to human FGFR4. The antibodies show advantageous properties with respect to their binding specificity and biological activity, in particular with respect to their capability to decrease cell growth and cell migration, their ability to activate a further antineoplastic agent and/or sensitize tumor cells to a therapeutic treatment. However, there still remains a need for new, effective therapies for treating hyperproliferative diseases, in particular cancer.

Sorafenib is a dual-action Raf kinase and VEGFR inhibitor that inhibits tumor cell proliferation and angiogenesis. Although originally developed as a Raf kinase inhibitor, it was subsequently found to inhibit a variety of kinase receptors, including VEGFR, EGFR, and PDGFR kinases (Wilhelm et al. (2004), Cancer Res 64: 7099-7109, Strumberg et al. (2005), *J Clin Oncol* 23: 965-972). Sorafenib has significant activity in four different tumor types, including renal, colon, pancreatic, lung, and ovarian tumors.

In the present invention it was surprisingly found, that a combination of certain anti-FGFR4 antibodies and Sorafenib represents a new and promising approach to cancer therapy. The combination treatment provides additive or even synergistic anticancer activity, thus leading to beneficial clinical effects.

Thus, a first aspect of the present invention is a combination of
(i) a human anti-FGFR4 antibody or a functional fragment of said antibody and
(ii) Sorafenib or a pharmaceutically acceptable salt thereof, for use in the prevention and/or treatment of a hyperproliferative disease associated with FGFR4 expression, overexpression and/or hyperactivity, wherein the human anti-FGFR4 antibody or the functional fragment of said antibody is directed against an epitope between amino acids 119-248, preferably between amino acids 152-240, more preferably between amino acids 230 and 240 of human FGFR4 (SEQ ID NO. 70).

In terms of the present invention, the term "antibody" particularly refers to molecules comprising at least one immunoglobulin heavy chain and at least one immunoglobulin light chain. Each heavy and light chain may comprise a variable and a constant domain. The antigen binding site may be formed from the variable domains of a heavy and light chain. A variable region (also referred to as variable domain) comprises complementarity determining regions (CDRs), e.g. a CDR1, a CDR2 and a CDR3 region and framework regions (FRs) flanking the CDRs. The term "complementarity determining region" is readily understood by the skilled person (see for example Harlow and Lane (eds), *Antibodies: A Laboratory Manual*, CSHL press, Cold Spring Harbor, N.Y., 1988) and refers to the stretches of amino acids within the variable domain of an antibody that primarily make contact with the antigen and determined antibody specificity. This region is also known as the hypervariable region.

The term "human antibody" encompasses fully human or humanized antibodies, wherein fully human antibodies are preferred. Human antibodies may be prepared from genetically engineered animals, e.g. animals comprising a xenogenic immune system or from antibody display libraries according to known techniques. Human antibodies are described generally in van Dijk and van de Winkel (*Curr. Opin. Pharmacol.* 5: 368-74 (2001)) and Lonberg (*Curr. Opin. Immunol.* 20: 450-459 (2008)). Human antibodies may be prepared by administering an immunogen to a transgenic animal that has been modified to produce intact human antibodies or intact antibodies with human variable regions in response to antigenic challenge Such animals typically contain all or a portion of the human immunoglobulin loci, which replace the endogenous immunoglobulin loci, or which are present extrachromosoally or integrated randomly into the animal's chromosomes. In such transgenic mice, the endogenous immunoglobulin loci have generally been inactivated. For review of methods for obtaining human antibodies from transgenic animals, see for example Lonberg, *Nat. Biotech.* 23: 1117-125 (200). Human variable regions from intact antibodies generated by such animals may be further modified, e.g. by combining with a different human constant region.

Human antibodies can also be made by hybridoma-based methods. Human myeloma and mouse-human heteromyeloma cell lines for the production of human monoclonal antibodies have been described (see e.g. Kozbor *J. Immunol.* 133: 3001 (1984); Brodeur et al., *Monoclonal Antibody Production Techniques and Applications*, pp, 51-63) Human antibodies generated via human B-cell hybridom technogy are also described in Li et al, *Proc. Natl. Acad. Sci., USA* 103: 3557-3562 (2006.

Human antibodies may also be generated by phage display methods (see e.g., U.S. Pat. Nos. 6,248,516, 5,403,484, 5,969,108, 5,885,793, 6,696,248, 8,49,500). Techniques for selecting human antibodies from antibody libraries are known in the art (see e.g., Carmen, S. et al., Briefings in Functional Genomics and Proteomics (2002) 1 (2), p. 189-203; and Siriwardena, D et a, Ophthalmology (2002) 109 (3) p. 427-431). For example, a phage display method can be used, which involves causing human antibody variable regions to be expressed as a single-chain antibody (scFv) on phage surface and selecting phages binding to antigens (Nature (1991), 352, (633), p. 624-628, Journal of Molecular Biology (1992), 227, (2), p 381-88, and Nature Biotechnology (2005), 23, (9), p. 1105-1116) Likewise, another phage display method can also be used, which involves causing human antibody Fab (antigen-binding fragment) to be expressed on the surface of phage and selecting phages binding to antigens (WO 97/08320 and WO 01/05950) Genes of the phages selected based on antigen binding can be analyzed to thereby determine DNA sequences encoding human antibody variable regions binding to the antigens. When the DNA sequence of scFv or Fab binding to the antigens is clarified. CDR sequences are extracted therefrom, and expression vectors having the sequences can be prepared and introduced into appropriate hosts, followed by gene expression to obtain human antibodies (WO 92/01047, WO 92/20791, WO 93/06213, WO 93/11236, WO 93/19172, WO 95/01438, WO 95/15388, Annu. Rev. Immunol (1994) 12, p. 433-455, and Nature Biotechnology (2005) 23 (9), p. 1105-1116).

Human antibodies may also be generated by isolating Fv clone variable domain sequences selected from human-derived phage display libraries. Such variable domain sequences may then be combined with a desired human constant domain Techniques for selecting human antibodies from antibody libraries are known n the art.

Humanized antibodies may be prepared by humanization of monoclonal antibodies according to known techniques. Typically, a non-human antibody is humanized to reduce immunogenicity to humans, while retaining the specificity and affinity of the parental non-human antibody. Humanized antibodies and methods of making them are reviewed, e.g. in Alamagro and Fransson, *Front Biosci.* 13: 1619-1633 (2008).

The invention also encompasses functional fragments of human antibodies, e.g., portions of the above-mentioned antibodies which comprise at least one antigen binding site. The term "functional fragment" as used herein is used with the same meaning as "antigen binding fragment" Examples of antibody functional fragments include Fab fragments, Fab fragments. F(ab')$_2$ fragments, FV fragments, diabodies or single chain antibody molecules and other fragments as tong as they exhibit the desired capability of binding to human FGFR4. For a review of certain antibody fragments see Hudson et al., Nat. Met. 9: 129-134 (2003).

Diabodies are antibody fragments with two antigen binding sites that may be bivalent or bispecific. See for example Hudson et al., (2003). Single-chain antibodies are antibody fragments comprising all or a portion of the heavy chain variable domain or all, or a portion of the light chain variable domain of an antibody. Antibody fragments can be made by Various techniques including but not limited to proteolytic digestion of an intact antibody as well as production by recombinant hosts (e.g. *E. coli* or phage) as described herein.

In certain embodiments, an antibody for the use provided herein is a multispecific antibody, e.g. a bispecific antibody. Multispecific antibodies are monoclonal antibodies that have binding specificities for at least two different sites.

In certain embodiments, one of the binding specifities is for FGFR4 and the other is for any other antigen.

In certain embodiments, bispecific antibodies may bind to two different epitopes of FGFR4. Bispecific antibodies may also be used to localize cytotoxic agents to cells which express FGFR4. Bispecific antibodies can be prepared as full-length antibodies or antibody fragments.

Techniques for making multispecific antibodies include but are not limited to recombinant co-expression of two immunoglobulin heavy chain-light chain pairs having different specificities and "knob in hole" engineering. Multispecific antibodies may also be made by engineering electrostatic steering effects for making antibody Fc-heterodimeric molecules crosslinking two or more antibodies or fragments; using leucine zippers to produce bispecific antibodies; using "diabody" technology for making bispecific antibodies and using single-chain Fv and preparing trispecific antibodies as described. Engineered antibodies with three or more functional antigen binding sites including "octopus antibodies" are also included herein.

In certain embodiments, amino acid sequence variants of the antibodies provided herein are contemplated as long as they exhibit the desired capability of binding to human FGFR4. For example, it may be desirable to improve the binding affinity and/or other biological properties of the antibody.

Amino acid sequence variants of an antibody may be prepared by introducing appropriate modifications into the nucleotide sequence encoding the antibody, or by peptide synthesis. Such modifications include, for example, deletions from and/or insertions into and/or substitutions of residues within the amino acid sequences of the antibody. Any combination of deletion, insertion and substitution can be made to arrive at the final construct, provided that the final construct possesses the desired characteristics, e.g. antigen binding. The number of amino acid residues to be deleted, inserted into, and/or substituted is generally 10 or less, preferably 5 or fewer, more preferably 3 or fewer, and most preferably 1 or 2.

The term "bind" or "binding" of an antibody means an at least temporary interaction or association with or to a target antigen, i.e., human FGFR4 comprising fragments thereof containing an epitope.

In certain embodiments, an antibody for the use provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-3}$ M or less, e.g. from $10^{-3}$ M to $10^{-13}$ M, e.g. $10^{-3}$ M to $10^{13}$M). In one embodiment, Kd is measured by a radiolabeled antigen binding assay (Radioimmunoassay, RIA) performed with the Fab version of an antibody of interest and its antigen.

According to another embodiment, Kd is measured using surface plasmon resonance assays with immobilized antigen According to a preferred embodiment of the present invention, the antibodies are human monoclonal antibodies directed against an epitope of human FGFR4 as described herein.

The antibodies or functional fragments thereof for the use of the present invention are directed against an epitope between amino acids 119-284 of human FGFR4. The epitope is preferably located in the Ig-like domain 2 of human FGFR4. The antibodies are described in more detail in international application PCT/EP2015/068440, the disclosure of which is incorporated herein by reference. Particularly preferred are human antibodies directed against an epitope between amino acids 152-240 and more preferably between amino acids 230 and 240 of human FGFR4. The epitope can be a conformational or a sequential epitope. Preferably, the antibodies for use according to the invention bind to a sequential epitope between amino acids 152-240 and more preferably between amino acids 230 and 240 of human FGFR4. According to a particularly preferred embodiment, the antibody for the use of the invention is directed against an epitope, preferably a sequential epitope, comprising, essentially consisting of or consisting of the amino acid sequence RYNY (SEQ ID NO. 69).

The antibodies for the use of the invention may be of various immunoglobulin (Ig) types, for example of the IgA-, IgD-, IgE-, IgG- or IgM-type, preferably of the IgG- or IgM-type including but not limited to the IgG1-, IgG2-, IgG3-, IgG4-, IgM1 and IgM2-type. In one preferred embodiment the antibody is of the IgG1-type.

In certain embodiments of the present invention, the antibody may comprise specific heavy chain complementarity determining regions CDRH1, CDRH2 and/or CDRH3 as described herein below.

In one embodiment, the human antibody comprises a heavy chain complementarity determining region 1 (CDRH1) having the amino acid sequence as shown in any one of SEQ ID NOs: 1-6, or an amino acid sequence differing in 1 or 2 amino acids therefrom.

In a further embodiment, the antibody comprises a heavy chain complementarity determining region 2 (CDRH2) having the amino acid sequence as shown in any one of SEQ ID NOs: 7-12, or an amino acid sequence differing in 1 or 2 amino acids therefrom.

In yet a further embodiment, the antibody comprises a heavy chain complementarity determining region 3 (CDRH3) having the amino acid sequence as shown in any one of SEQ ID Nos: 13-20, or an amino acid sequence differing in 1 or 2 amino acids therefrom.

The antibody according to the invention may also comprise specific light chain complementarity determining regions CDRL1, CDRL2 and/or CDRL3.

Accordingly, in one embodiment, the antibody comprises alight chain complementarity determining region 1 (CDRL1) having the amino acid sequence as shown in any one of SEQ ID NOs: 21-23 and 68, or an amino acid sequence differing in 1 or 2 amino acids therefrom.

In a further embodiment, the antibody comprises a light chain complementarity determining region 2 (CDRL2) having the amino acid sequence as shown in any one of SEQ ID NOs: 24-27, or an amino acid sequence differing in 1 or 2 amino acids therefrom.

In yet a further embodiment, the antibody comprises a light chain complementarity determining region 3 (CDRL3) having the amino acid sequence as shown in any one of SEQ ID NOs:2835, or an amino acid sequence differing in 1 or 2 amino acids therefrom.

The antibody may preferably comprise a specific combination of CDRs (i.e. of CDRH1 CDRH2 and CDRH3) within one heavy chain.

Accordingly, in one preferred embodiment, the antibody comprises a heavy chain comprising complementarity determining regions CDRH1, CDRH2 and CDRH3, wherein CDRH1 is selected from the sequences as shown in SEQ ID NOs: 1-6, or an amino acid sequence differing in 1 or 2 amino acids therefrom, CDRH2 is selected from the sequences shown in SEQ ID NOs: 7-12, or an amino acid sequence differing in 1 or 2 amino acids therefrom, and CDRH3 is selected from the sequences shown in SEQ ID NOs: 13-20, or an amino acid sequence differing in 1 or 2 amino acids therefrom.

Most preferably, the antibody for the use of the invention comprises a heavy chain comprising three CDRs, wherein the combination of CDRH1, CDRH2 and CDRH3 is selected from those shown in table 1. It is understood that each line of this table represents one specific combination of a CDRH1, a CDRH2 and a CDRH3.

TABLE 1

| CDRH1 | CDRH2 | CDRH3 |
|---|---|---|
| RNYMS (SEQ ID NO. 1) | AISGSGGSTYYADSVKG (SEQ ID NO. 7) | VTSPGAFDI (SEQ ID NO. 13) |
| KAWMS (SEQ ID NO. 2) | AISGSGGSTYYADSVKG (SEQ ID NO. 7) | LYSYGDFDH (SEQ ID NO. 14) |
| DYYMS (SEQ ID NO. 3) | TISGSGGSTYYADSVKG (SEQ ID NO. 8) | LTAYGHVDS (SEQ ID NO. 15) |
| SNYMS (SEQ ID NO. 4) | LISGSGGSTYYADSVQG (SEQ ID NO. 9) | NTAGFGYFDL (SEQ ID NO. 16) |
| SNYMN (SEQ ID NO. 5) | VISYDGSNKYYADSVKG (SEQ ID NO. 10) | KSRDFWRGPFDY (SEQ ID NO. 17) |
| SNYMS (SEQ ID NO. 4) | SISGSGGRTYYADSVKG (SEQ ID NO. 11) | MTVFGAATL (SEQ ID NO. 18) |
| DYYMN (SEQ ID NO. 6) | AIGGSGDRTYYADSVKG (SEQ ID NO. 12) | GGSYFGY (SEQ ID NO. 19) |
| DYYMS (SEQ ID NO. 3) | AISGSGGSTYYADSVKG (SEQ ID NO. 7) | LATYGPFDD (SEQ ID NO. 20) |

According to the present invention, it is further preferred that the antibody comprises a specific combination of CDRs within one light chain (i.e. of CDRL1, CDRL2 and CDRL3).

Thus, in one preferred embodiment, the antibody comprises a light chain comprising complementarity determining regions CDRL1, CDRL2 and CDRL3, wherein CDRL1 has the amino acid sequence as shown in any of SEQ ID NOs:22-3 and 68, or an amino acid sequence differing in 1 or 2 amino acids therefrom, CDRL2 has the amino acid sequence as shown in any of SEQ ID NOs: 24-27, or an amino acid sequence differing in 1 or 2 amino acids therefrom, and CDRL3 has the amino acid sequence as shown in any of SEQ ID NO: 28-35, or an amino acid sequence differing in 1 or 2 amino acids therefrom.

Most preferably, the antibody for the use of the invention comprises a light chain comprising three CDRs, wherein the combination of CDRL1, CDRL2 and CDRL3 is selected from those shown in table 2. It is understood that each line of this table represents one specific combination of a CDRL1, a CDRL2 and a CDRL3.

TABLE 2

| CDRL1 | CDRL2 | CDRL3 |
|---|---|---|
| SGGTSNIGTNTVN (SEQ ID NO. 21) | RNNQRPS (SEQ ID NO. 24) | AAWDDSLNGPYVV (SEQ ID NO. 28) |
| SGSSSNIGSNTVN (SEQ ID NO. 22) | RNNQRPS (SEQ ID NO. 24) | AAWDDSLNGPAVV (SEQ ID NO. 29) |
| SGSSSNIGTNTVN (SEQ ID NO. 23) | RNYQRPS (SEQ ID NO. 25) | AAWDDSLSGPHVV (SEQ ID NO. 30) |

TABLE 2-continued

| CDRL1 | CDRL2 | CDRL3 |
|---|---|---|
| SGSSSNIGSNTVN (SEQ ID NO. 22) | RNNQRPS (SEQ ID NO. 24) | AAWDDSLNGPLVV (SEQ ID NO. 31) |
| SGSSSNIGSNTVN (SEQ ID NO. 22) | RNNQRPS (SEQ ID NO. 24) | STWDDSLRGWV (SEQ ID NO. 32) |
| SGSSSNIGSNTVN (SEQ ID NO. 22) | RNNQRPS (SEQ ID NO. 24) | AAWDDSLNGPYWV (SEQ ID NO. 33) |
| SGSSSNIGSNTVN (SEQ ID NO. 22) | YDDLLPS (SEQ ID NO. 26) | AAWDDSLNGPV (SEQ ID NO. 34) |
| SGSSSNIGSNTVH (SEQ ID NO. 68) | RNNRRPS (SEQ ID NO. 27) | AAWDDSLSGPNVV (SEQ ID NO. 35) |

As described above, the complementarity determining regions (CDRs) of an antibody may be flanked by framework regions. A heavy or light chain of an antibody containing three CDRs contains e.g. four framework regions.

Additionally, the present invention also encompasses those antibodies that recognize the same epitope on human FGFR4 as a specific antibody characterized by the above heavy and/or light chain CDRs, Functional fragments of those antibodies are also within the scope of the invention. To determine the epitope on FGFR4 recognized by the antibody, chemically Prepared arrays of protein sequence derived short peptides derived from the amino acid sequence of the extracellular domain of human FGFR4 can be used to locate and identify antibody epitopes (Reinicke W., *Methods Mol. Biol.* 2004, 248: 443-63). A further method to map the epitopes in the FGFR4 extracellular domain bound by the antibodies of the invention comprises Snaps/SELDI (Wang et al., Int. J. Cancer, 2001, June 15; 92 (6): 871-6) or a routine cross-blocking assay Such as described in Antibodies, *A Laboratory Manual*, Cold Spring Harbor Laboratory, Ed Harlow and David Lane (1988) can be performed.

According to a particularly preferred embodiment, the human antibody for use of the invention comprises a heavy chain comprising at least one CDR selected from the group consisting of (a) a CDRH1 as shown in SEQ ID NO: 1-6, or a CDRH1 sequence differing in 1 or 2 amino acids therefrom,
(b) a CDRH2 as shown in SEQ ID NO: 7-12, or a CDRH2 sequence differing in 1 or 2 amino acids therefrom, and
(c) a CDRH3 as shown in SEQ ID NO: 13-20, or a CDRH3 sequence differing in 1 or 2 amino acids therefrom,
and/or a light chain comprising at least one CDR selected from the group consisting of
(d) a CDRL1 as shown in SEQ ID NO: 21-23 or 68, or a CDRL1 sequence differing in 1 or 2 amino acids therefrom,
(e) a CDRL2 as shown in SEQ ID NO: 24-2, or a CDRL2 sequence differing in 1 or 2 amino acids therefrom, and
(f) a CDRL3 as shown in SEQ ID NO 28-35, or a CDRL3 sequence differing in 1 or 2 amino acids therefrom.

In a preferred embodiment of the invention, the human antibody comprises a heavy chain variable region (VH) as shown in any one of SEQ 10 NOs. 52-59 or a sequence differing in 1 or 2 amino acids therefrom. Furthermore, the human antibody of the invention preferably comprises a light chain variable region (VL) as shown in any one of SEQ ID NOs. 60-67 or a sequence differing in 1 or 2 amino acids therefrom, Particularly preferred are human antibodies comprising a heavy chain variable region as shown in any one of SEQ ID NOs 52-59 and a light chain variable region as shown in in any one of SEQ ID NOs, 60-67.

Particularly preferred is a human antibody (U4-1) comprising a heavy chain comprising a CDRH1 as shown in SEQ ID NO: 1, a CDRH2 as shown in SEQ ID NO: 7 and a CDRH3 as shown in SEQ ID NO: 13 and a light chain comprising a CDRL1 as shown in SEQ ID NO: 21, a CDRL2 as shown in SEQ ID NO: 24 and a CDRL3 as shown in SEQ ID NO: 28. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 52 and a light chain variable region according to SEQ ID NO: 60. Also encompassed are human antibodies wherein the sequences of the variable region of the heavy chain and/or the light chain differ in 1 or 2 amino acids from those shown in SEQ ID NOs, 52 and 60.

Particularly preferred is a human antibody (U4-2) comprising a heavy chain comprising a CDRH1 as shown in SEQ ID NO: 2, a CDRH2 as shown in SEQ ID NO: 7 and a CDRH3 as shown in SEQ ID NO:14 and a light chain comprising a CDRL1 as shown in SEQ ID NO: 22, a CDRL2 as shown in SEQ ID NO: 24 and a CDRL3 as shown in SEQ ID NO: 29. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 53 and a light chain variable region according to SEQ ID NO: 61. Also encompassed are human antibodies wherein the sequences of the variable region of the heavy chain and/or the light chain differ in 1 or 2 amino acids from those shown in SEQ ID NOs. 53 and 61.

Particularly preferred is a human antibody (U4-3) comprising a heavy chain comprising a CDRH1 as shown in SEQ ID NO:3, a CDRH2 as shown in SEQ ID NO: 8 and a CDR as shown in SEQ ID NO: 15 and a light chain comprising a CDRL1 as shown in SEQ ID NO 23, a CDRL2 as shown in SEQ ID NO: 25 and a CDRL3 as shown in SEQ ID NO: 30. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO:54 and a light chain variable region according to SEQ ID NO: 62. Also encompassed are human antibodies wherein the sequences of the variable region of the heavy chain and/or the light chain differ in 1 or 2 amino acids from those shown in SEQ ID NOs. 54 and 62.

Particularly preferred is a human antibody (U4-4) comprising a heavy chain comprising a CDRH1 as shown in SEQ ID NO: 4, a CDRH2 as shown in SEQ ID NO: 9 and a CDRH3 as shown in SEQ ID NO: 16 and a light chain comprising a CDRL1 as shown in SEQ ID NO; 22, a CDRL2 as shown in SEQ ID NO: 24 and a CDRL3 as shown in SEQ ID NO: 31. Also encompassed are human antibodies, wherein one or more of the CDR differ in 1 or 2 amino acids or antibodies recognizing the same epitope on human FGFR4, In a particularly preferred embodiment, the human antibody comprises a heavy chain variable region according to SEQ ID NO: 55 and a light chain variable region according to SEQ D NO: 63. Also encompassed are human antibodies wherein the sequences of the variable region of the heavy chain and/or the light chain differ in 1 or 2 amino acids from those shown in SEQ ID NOs. 55 and 63.

Particularly preferred is a human antibody (U4-5) comprising a heavy chain comprising a CDRH1 as shown in SEQ ID NO: 5, a CDRH2 as shown in SEQ ID NO: 10 and a CDRH3 as shown in SEQ ID NO: 17 and a light chain comprising a CDRL1 as shown in SEQ ID NO: 22, a CDRL2 as shown in SEQ ID NO: 24 and a CDRL3 as shown in SEQ ID NO: 32, Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 56 and a light chain variable region according to SE D NO: 64. Also encompassed are human antibodies wherein the sequences of the variable region of the heavy chain and/or the light chain differ in 1 or 2 amino acids from those shown in SEQ ID NOs. 56 and 64.

Particularly preferred is a human antibody (U4-6) comprising a heavy chain comprising a CDRH1 as shown in SEQ ID NO:6, a CDRH2 as shown in SEQ ID NO: 12 and a CDRH3 as shown in SEQ ID NO: 19 and a light chain comprising a CDRL1 as shown in SEQ ID NO: 22, a CDRL2 as shown in SEQ ID NO: 26 and a CDRL3 as shown in SEQ ID NO: 34. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 58 and a light chain variable region according to SEQ ID NO: 66. Also encompassed are human antibodies wherein the sequences of the variable region of the heavy chain and/or the light chain differ in 1 or 2 amino acids from those shown in SEQ ID NOs, 58 and 66.

Particularly preferred is a human antibody (U4-7) comprising a heavy chain comprising a CDRH1 as shown in SEQ NO: 3, a CDRH2 as shown in SEQ ID NO: 7 and a CDRH3 as shown in SEQ ID NO: 20 and a light chain comprising a CDRL1 as shown in SEQ ID NO:68, a CDRL2 as shown in SEQ ID NO: 27 and a CDRL3 as shown in SEQ ID NO; 35. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 9 and a light chain variable region according to SEQ ID NO: 67. Also encompassed are human antibodies wherein the sequences of the variable region of the heavy chain and/or the light chain differ in 1 or 2 amino acids from those shown in SEQ ID NOs. 59 and 67.

Particularly preferred is a human antibody (U4-8) comprising a heavy chain comprising a CDRH1 as shown in SEQ ID NO 4, a CDRH2 as shown in SEQ ID NO: 11 and a CDRH3 as shown in SEQ ID NO: 18 and a light chain comprising a CDRL1 as shown in SEQ ID NO: 22, a CDRL2 as shown in SEQ ID NO: 24, and a CDRL3 as shown in SEQ ID NO: 33. Also encompassed are human antibodies, wherein one or more of the CDRs differ in 1 or 2 amino acids or antibodies recognizing the same epitope on human FGFR4. In a particularly preferred embodiment, the human antibody comprises a heavy chain variable region according to SEQ ID NO: 57 and a light chain variable region according to SEQ ID NO:65, Also encompassed are human antibodies wherein the sequences of the variable region of the heavy chain and/or the light chain differ in 1 or 2 amino acids from those shown in SEQ ID NOs. 57 and 6.

Also preferred is a human antibody (U4-9) comprising a heavy chain comprising a CDR1 as shown in SEQ ID NO:

3, a CDRH2 as shown in SEQ ID NO: 8 and a CDRH3 as shown in SEQ ID NO: 15 and a light chain comprising a CDRL1 as shown in SEQ ID NO: 68, a CDRL2 as shown in SEQ ID NO: 27 and a CDRL3 as shown in SEQ ID NO: 35. Also encompassed are human antibodies, wherein one or more of the CDRs differ in one or two amino acids or antibodies recognizing the same epitope on human FGFR4. In a particularly preferred embodiment the human antibody comprises a heavy chain variable region according to SEQ ID NO: 54 and a light chain variable region according to SEQ ID NO: 67. The antibody U4-9 preferably comprises the heavy chain as specified for antibody U4-3 and the light chain as specified for antibody U4-7. In the experiments provided in the application PCT/EP2015/068440, the antibody U4-9 proved to have a higher affinity for FGFR4 than 4-3.

In certain embodiments, the antibodies or functional fragments thereof for the use of the present invention include an antibody or afunctional fragment thereof, having substantial identity with a variable region of U4-1, U4-2; U4-U4-4, U4-5, U4-6, U4-7, U4-8 or U4-9 heavy chain or light chain variable region. The term "substantial identity" means that two amino acid sequences share at least 80% sequence identity, preferably at least 90%, more preferably at least 95% sequence identity, and most preferably at least 99% sequence identity. The identity between two amino acid sequences can be determined using Blast algorithm version 2.2.2 (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs" Nucleic Acids Res. 25: 3389-3402) with default parameters. The Blast algorithm can also be used through the Internet by accessing the site www.ncbi.nlm.nih.gov/blast.

In certain embodiments, the antibodies or functional fragments thereof for the use of the present invention include an antibody or a functional fragment thereof that competes with U4-1, U4-2, U4-3, U4-4, U4-5, U4-6, U4-7, U4-8 or U4-9 for the binding to FGFR4.

The antibodies for the use of the present invention can for example be obtained from nucleic acid molecules comprising nucleic acid sequences as shown in any one of SEQ ID NOs: 36-43 and SEQ ID NOs, 44-51 as described in more detail in co-pending application PCT/EP2015/068440.

As mentioned above, the human anti-FGFR4 antibodies show advantageous properties with respect to their binding specificity and biological activity, in particular with respect to their capability to recognize epitopes of the human FGFR4, to decrease cell growth and cell migration, their ability to activate a further antineoplastic agent and/or sensitize tumor cells to a therapeutic treatment. The antibodies of the invention U4-1 to U4-9 have intrinsic antitumor activity. They specifically bind to FGFR4 and preferably show no cross-reactivity to other FGF receptors FGFR1-3b, c.

The antibody for use of the present invention ay be coupled to a heterologous group, e.g. an effector group. Such an antibody conjugate is especially suitable for therapeutic applications. The term "effector group" may refer to a cytotoxic group, such as a radioisotope or a radionuclide, a toxin, a therapeutic group or another effector group known in the art. Conjugates wherein the antibody is coupled to a therapeutic group, so-called antibody-drug-conjugates (ADCs) are particularly preferred. Alternatively, the antibody may be coupled to a labeling group. Such an antibody conjugate is particularly suitable for diagnostic applications. As used herein, the term "labeling group" refers to a detectable marker, e.g. a radiolabeled amino acid or biotin moiety, a fluorescent marker, an enzyme or any other type of marker which is known in the art. The linking of antibodies or antibody fragments to radioisotopes e.g. provides advantages to tumor treatments. Unlike chemotherapy and other forms of cancer treatment, radoimmunotherapy or the administration of a radioisotope-antibody combination targets the cancer cells with minimal damage to surrounding normal healthy tissue.

A further embodiment of the present invention is a combination for the use as defined above, wherein the antibody is fused to interleukin-2 (IL-2). Interleukin-2 is a 1 kDa cytokine produced by T helper cells that stimulates cytotoxic T lymphocytes and NK cells. IL-2 has been used clinically in the treatment of melanoma and renal cell carcinoma to stimulate cancer patient's immune systems Achieving a prolonged high dose of IL-2 in the tumor can result in the induction of a long-lasting anti-tumor response leading to the rejection of an otherwise lethal tumor. In the present invention it has been found that it is possible to incorporate IL-2 into a fusion protein including an antibody as described herein above while maintaining its activity. Hence, a fusion protein wherein an antibody is fused to IL-2 is suitable to serve as a delivery system which retains antigen binding specificity and possesses the full activity of IL-2.

According to the present invention, the above defined antibodies are used in combination with Sorafenib or a pharmaceutically acceptable salt thereof.

The term "Sorafnib" refers to the small molecular inhibitor 4-[4-[[4-chloro-3-(trifiuoromethyl)phenyl]carbamnoylamnino]phenoxy]-N-methyl-pyridine-2-carboxamide.
Sorafenib and the preparation thereof are described inter alia in WO 00/42012 and WO 03/068228. It is understood that pharmaceutically acceptable salts of Sorafenib as well as commonly used prodrugs are also within the scope of the invention.

Pharmaceutically acceptable salts of Sorafenib are for example organic or inorganic acid addition salts. Suitable inorganic acids include but are not limited to halogen acids (such as hydrochloric acid and hydrobromic acid), sulfuric acid, or phosphoric acid. Suitable organic acids include but are not limited to carboxylic, phosphonic, sulfonic, or sulfamic acids, with examples including acetic acid, propionic acid, octanoic acid, decanoic acid, trifluoroacetic acid, dodecanoic acid, glycolic acid, lactic acid, 2- or 3-hydroxybutyric acid, γ-aminobutyric acid (GABA), gluconic acid, glucose-monocarboxylic acid, benzoic acid, salicylic acid, phenylacetic acid and mandelic acid, fumaric acid, succinic acid, adipic acid, pimelic acid, suberic acid, azeiaic acid, malic acid, tartaric, acid, citric acid, glucaric acid, galactaric acid, amino acids (such as glutamic acid, aspartic acid, N-methylglycine, acetytaminoacetic acid, N-acetylasparagine or N-acetylcysteine), pyruvic acid, acetoacetic acid, methane-sulfonic acid, tri-fluoromethane sulfonic acid, 4-toluene sulfonic acid, benzenesulfonic acid, 1-naphthalenesulfonic acid, 2-naphthalenesulfonic acid, phosphoserine, and 2- or 3-glycerophosphoric acid.

In addition, pharmaceutically acceptable salts include acid salts of inorganic bases, such as salts containing alkaline cations (e. g, Li+ Na+ or K+), alkaline earth cations (e, g, Mg+2, Ca+2 or Ba+2), the ammonium cation, as well as acid salts of organic bases, including aliphatic and aromatic substituted ammonium, and quaternary ammonium cations; such as those arising from protonation or peralkylation of triethylamine, N, N-diethylamine, N, N-dicyclohexylamine, lysine, pyridine, N, N-dimethylaminopyridine (DMAP), 1, 4-diazabiclo [2.2.2] octane (DABCO), 1,5-diazabicyclo [4.3.0] non-5-ene (DBN) and 1,8-diazabicyclo [5.4.0] undec-7-ene (DBU).

The formation of prodrugs is well known in the art in order to enhance the properties of the parent compound; such properties include solubility, absorption, biostability and release time (see "Pharmaceutical Dosage Form and Drug Delivery Systems" (Sixth Edition), edited by Ansel et al., published by Williams & Wilkins, pages 27-29, (1995) which is hereby incorporated by reference) Commonly used prodrugs of Sorafenib are designed to take advantage of the major drug biotransformation reactions and are also to be considered within the scope of the invention. Major drug biotransformation reactions include N-dealkylation, O-dealkylation, aliphatic hydroxylation, aromatic hydroxylation, N-oxidation, S-oxidation, deamination, hydrolysis reactions, glucuronidation, sulfation and acetylation (see Goodman and Gilman's The Pharmacological Basis of Therapeutics (Ninth Edition), editor Molinoff et al., pub. by McGraw-Hill, pages 11-13, (1996), which is hereby incorporated by reference).

In a preferred embodiment, a tosylate salt of Sorafenib is used. The scaleable synthesis of Sorafenib and its tosylate salt is disclosed in Organic Process Research and Development (2002), Vol. 6, Issue #6, 777-781, and WO 03/068228, which is incorporated herein by reference.

The usefulness of a combination of an anti-FGFR4 antibody as defined above with Sorafenib or a pharmaceutically acceptable salt thereof is better than could have been expected from conventional knowledge of the effects of using either agent alone. For example, the combination therapy of the antibody U4-3 with Sorafenib has produced at least additive anti-tumor efficacy compared with that produced by administration of either the antibody or Sorafenib administered alone. Generally, the use of the above defined anti-FGFR4 antibodies in combination with the raf kinase inhibitor Sorafenib will serve to yield better efficacy in reducing the growth of a tumor or even eliminate the tumor as compared to administration of a single agent, provide for the administration of lesser amounts of the administered agents, provide for a chemotherapeutic treatment that is well tolerated in the patient with less deleterious pharmacological complications resulting from larger doses of single chemotherapies and certain other combined therapies, provide for treating a broader spectrum of different cancer types in mammals, especially humans, provide for a higher response rate among treated patients, provide for a longer survival time among treated patients compared to standard chemotherapy treatments, provide a longer time for tumor progression, and/or yield efficacy and tolerability results at least as good as those of the agents used alone, compared to known instances where other cancer agent combinations produce antagonist effects.

According to the invention, the combination of (i) a human anti-FGFR4 antibody or a functional fragment of said antibody and (ii) Sorafenib or a pharmaceutically acceptable salt thereof is used in the prevention and/or treatment of hyperproliferative diseases associated with FGFR4 expression, overexpression and/or hyperactivity. In particular, the combination of the invention is for use in treating cancer including but not limited to colon cancer, colorectal carcinoma, prostate cancer, leukemia, melanoma, hepatocellular carcinoma (HCC), renal cell carcinoma (RCC), head and neck cancer, glioma, lung cancer, pancreatic cancer, ovarian cancer, and mammary carcinoma. Examples for diseases that can be prevented and/or treated using an antibody of the invention are detailed below.

For the combination according to the present invention, the human anti-FGFR4 antibody and/or Sorafenib can be provided as a common pharmaceutical preparation or, more preferred, as separate pharmaceutical preparations, each optionally including a pharmaceutically acceptable carrier.

The term "carrier" includes agents, e.g. diluents, stabilizers, adjuvants or other types of excipients that are non-toxic to the cell or mammal to be exposed thereto at the dosages and concentrations employed. Examples of pharmaceutically acceptable carriers are well-known in the art and include phosphate-buffered saline solutions, water, emulsions such as oil/water emulsions, various types of wetting agents, sterile solutions, etc. Often the pharmaceutically acceptable carrier is an aqueous pH-buffered solution which is useful for drug delivery, particularly for the delivery of antibody molecules. The pharmaceutical compositions may be formulated by well-known conventional methods, i.e. by mixing the active agent with carriers and optionally other agents that are usually incorporated into the formulation. For example, the composition may be formulated in the form of lyophilized formulations, aqueous solutions, dispersions or solid preparations.

Administration of the suitable compositions may be effected by different ways, e.g. by intravenous, intraperitoneal subcutaneous, intramuscular, topical, intradermal, intranasal or intrabronchial administration. The compositions may also be administered directly to the target site, e.g. by biolistic delivery to an external or internal target site, like the brain. The dosage regimen will be determined by the attending physician and clinical factors.

In a preferred embodiment, compositions comprising the anti-FGFR4-antibody and/or Sorafenib or a pharmaceutically acceptable salt thereof can be administered to a patient by oral delivery or by intravenous injection or infusion.

In another preferred embodiment compositions comprising the anti-FGFR4-antibody and/or Sorafenib or a pharmaceutically acceptable salt thereof can be administered to a patient in the form of a tablet, a liquid, a topical gel, an inhaler or in the form of a sustained release composition.

The anti-FGFR4-antibody can be administered simultaneously with Sorafenib or a pharmaceutically acceptable salt thereof to a patient, in the same formulation or, more typically in separate formulations and, often, using different administration routes. Administration can also be sequentially, in any order.

In a preferred embodiment, the anti-FGFR4 antibody or afunctional fragment of said antibody can be administered in tandem with Sorafenib or a pharmaceutically acceptable salt thereof wherein the anti-FGFR4 antibody or a functional fragment of said antibody can be administered to a patient once or more per day for up to 28 consecutive days with the concurrent or intermittent administration of Sorafenib or a pharmaceutically acceptable salt thereof over the same total time period.

The combinations of the invention can also be formed in vivo, e. g., in a patients body.

Pharmaceutical preparations containing the above defined anti-FGFR4 antibodies and/or Sorafenib or a pharmaceutically acceptable salt thereof can be administered orally, dermally, parenterally, by injection, by inhalation or spray, sublingually, rectally or vaginally in dosage unit formulations. The term "administration by injection" includes intravenous, intraarticular, intramuscular, subcutaneous and parenteral injections, as well as use of infusion techniques. Dermal administration may include topical application or transdermal administration, One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations, Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active material in admixture with excipients suitable for the manufacture of aqueous suspensions may also be used, Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for examples sweetening, flavoring and coloring agents, may also be present.

The compounds may also be in the form of non-aqueous liquid formulations, e. g., oily suspensions which may be formulated by suspending the active ingredients in polyethyleneglycol, a vegetable oil, for example arachis oil olive oil, sesame oil or peanut oil, or in a mineral oil such as liquid paraffin. The oily suspensions may contain a thickening agent, for example beeswax, hard paraffin or cetyl alcohol Sweetening agents such as those set forth above, and flavoring agents may be added to provide palatable oral preparations. These compositions may be preserved by the addition of an anti-oxidant such as ascorbic acid.

Pharmaceutical compositions for the use of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agent.

The compounds may also be administered in the form of suppositories for rectal or vaginal administration of the drug. These compositions can be prepared by mixing the drug with a suitable non-irritating excipient which is solid at ordinary temperatures but liquid at the rectal temperature or vaginal temperature and will therefore melt in the rectum or vagina to release the drug. Such materials include cocoa butter and polyethylene glycol. Compounds of the invention may also be administrated transdermally using methods known to those skilled in the art (see, for example: Chien; "Transdermal Controlled Systemic Medications"; Marcel Dekker. Inc.; 187. Lipp et at W094/04167), For example, a solution or suspension of Sorafenib or a pharmaceutically acceptable salt thereof in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of Sorafenib or a pharmaceutically acceptable salt thereof may be formulated into a lotion or salve.

Suitable solvents for processing transdermal delivery systems are known to those skilled in the art, and include dimethylsulfoxide, lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluorethane, or trichlorofluoroethane. Suitable solvents may also include mixtures of one or more materials selected from lower alcohols, lower ketones, lower carboxylic acid esters polar ethers, lower hydrocarbons, halogenated hydrocarbons.

Suitable penetration enhancing materials for transdermal delivery systems are known to those skilled in the art, and include, for example monohydroxy or polyhydroxy alcohols such as ethanol, propylene glycol or benzyl alcohol, saturated or unsaturated fatty alcohols such as lauryl alcohol or cetyl alcohol, saturated or unsaturated fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to 24 carbons such as disopropyl adipate, diisobutyl adipate, diisopropyl sebacate, diisopropyl maleate or diisopropyl fumarate. Additional penetration enhancing materials include phosphatidyl derivatives such as lecithin or cephalin, terpenes, amides, ketones, ureas and their derivatives, and ethers such as dimethyl isosorbid and diethylenegycol monoethyl ether. Suitable penetration enhancing formulations may also include mixtures of one or more materials selected from monohydroxy or polyhydroxy alcohols, saturated or unsaturated C8-C18 fatty alcohols, saturated or unsaturated Cg-Cig fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers. Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes and silicates may also be used as matrix components. Additional additives, such as viscous resins or oils may be added to increase the viscosity of the matrix.

The invention also encompasses kits for treating hyperproliferative diseases associated with FGFR4 expression, overexpression and/or hyperactivity, in particular mammalian cancers. The kit can comprise a single pharmaceutical formulation containing an effective dose of an anti-FGFR4 antibody or a functional fragment of said antibody and an effective dose of Sorafenib or a pharmaceutically acceptable salt thereof. Alternatively, the kit can comprise an effective dose of an anti-FGFR4 antibody or a functional fragment of said antibody and an effective dose of Sorafenib or a pharmaceutically acceptable salt thereof in separate formulations. The kit can also include instructions for how to administer the compounds to a patient in need of treatment. The kit can be used to treat different hyperproliferative diseases associated with FGFR4 expression, overexpression and/or hyperactivity as described in more detail below. The kit is particularly suitable for treating cancer including but not limited to colon cancer, colorectal carcinoma, prostate cancer, leukemia, melanoma, hepatocellular carcinoma (HCC), renal cell carcinoma (RCC), head and neck cancer, glioma, lung cancer, pancreatic cancer, ovarian cancer, and mammary carcinoma.

It will be appreciated by those skilled in the art that the particular method of administration of the combination of the invention will depend on a variety of factors, all of which are routinely considered when administering therapeutics. It will also be understood, however, that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy, it will be further appreciated by one skilled in the art that the optimal course of treatment, i. e., the mode of treatment and the daily number of doses of the anti-FGFR4 antibody and Sorafenib or a pharmaceutically acceptable salt thereof given for a defined number of days can be ascertained by those skilled in the art using conventional treatment tests.

Depending on the type and severity of the condition to be treated, about 1 μg/kg to 15 mg/kg of the active ingredients may be administered to a patient in need thereof, e. g. by one or more separate administrations or by continuous infusion. A typical daily dose might range from about 1 μg/kg to about 100 mg/g, depending on the factors mentioned above. For repeated administrations over several days or longer, depending on the condition to be treated, the treatment is sustained until a desired suppression of the disease or the symptoms occurs. The composition may be administered by any suitable route, for example by parental, subcutaneous, intranasal, intravascular, intravenous, intra-arterial or intrathecal injection or infusion. Progress can be monitored by periodic assessment. The compositions may be administered locally or systemically. For example, the effective dose of Sorafenib may be, but not limited to, 400 mg (2×200 mg tablets) taken tice daily.

The combination according to the present invention may be administered together with other active agents. The additional active agent(s) may be administered separately or as a part of a common pharmaceutical composition.

According to a preferred embodiment, the combination treatment of the invention may comprise administering further agents. Examples for further active agents include an additional antineoplastic agent, small-molecule inhibitor, anti-tumor agent or chemotherapeutic agent. Such combination is effective for example in inhibiting abnormal cell growth.

Many antineoplastic agents are presently known in the art. In one embodiment, the antineoplastic agent is selected from the group of therapeutic proteins including but not limited to antibodies or immunomodulatory proteins.

In another embodiment, the antineoplastic agent is selected from the group of small-molecule inhibitors or chemotherapeutic agents consisting of mitotic inhibitors, kinase inhibitors, alkylating agents, antimetabolites, intercalating antibodies, growth factor inhibitors, cell cycle inhibitors, enzymes, topoisomerase inhibitors, histone deacetylase inhibitors, anti-survival agents, biological response modifiers, anti-hormones, e.g. anti-androgens and anti-angiogenesis agents.

The above-mentioned additional active agents can, of course, not only be administered together with the anti-FGFR4 antibody and/or Sorafenib within a mutual pharmaceutical composition, but they can also be administered separately.

In an additional embodiment, the present invention relates to a method of treating hyperproliferative diseases associated with FGFR4 expression, overexpression and/or hyperactivity.

According to the present invention, hyperproliferative diseases associated with FGFR4 expression overexpression and/or hyperactivity include for example cancer, Cancer that can be p vented and/or treated according to the invention may be selected from the group consisting of hepatocellular carcinoma (HCC), mammary carcinoma, colon cancer, colorectal carcinoma, leukemia, rhabdomyosarcoma, prostate cancer, ovarian cancer, soft tissue sarcoma, melanoma, head-and-neck squamous cell carcinoma (HNSCC). pancreatic cancer, renal cell carcinoma (RCC), lung cancer, (e.g. lung adenocarcinoma), glioma and other FGFR4-expressing or -overexpressing cancers and formation of tumor metastases. The combination of the invention proved to be particularly effective in treating hepatocellular carcinoma (HCC), renal cell carcinoma (RCC), and thyroid cancer.

The present invention shall be explained in more detail by the following figures and examples.

FIGURE LEGENDS

EXAMPLES

Example 1

In Vivo Growth Inhibition of Huh-7 Liver Cancer Cells

Human hepatocarcinoma model HuH-7 (Japanese Collection of Research Bioresources, Lot Nr.: 03282011) was implanted subcutaneously (s.c) into the right flank of weeks of age nu/nu athymic female mice (Charles River Laboratories, Japan) at $5 \times 10^6$ cells per animal suspended in 100 µl Matrigel.

Allocation group for therapy was performed 12 to 15 days after HuH-7 ce suspension implantation, when implanted tumours reached an average tumour volume of 200 mm$^3$. Tumor volume was measured with a digital caliper (Mitutoyo Corporation CD-15CX) and calculated according to the formula: Estimated tumour volume $(mm^3) = \frac{1}{2} \times length \times width^2 \cdot 10$ mice were randomized per group.

Therapy with Sorafenib and FGFR4 inhibitor U4-3 as single therapy agent or in co-administration started the same day immediately after group allocation of the animals into the study experimental group.

For the therapy with Sorafenib and 4-3 as single therapy agent and in co-administration, dosing solution of Sorafenib and U4-3 was prepared freshly every dosing time point using as solvent Cremophor EL/ethanol 95% water (12.5:12.5:75) and PBS, respectively. The formulation solution of each compound was adjusted to an appropriate concentration of the active compound for each therapy group and a final dosing volume of 10 ml/kg.

Sorafenib as single agent therapy or in co-administration with U4-3 was administered orally (p.o.) with a daily frequency at doses of 10 and 30 mg/kg and for 10 consecutive days.

U4-3 as single agent therapy or in co-administration with Sorafenib was administered intraperitoneally (i.p) twice weekly (2qW) at doses of 3, 10 and 25 mg/kg for a period of time of 10 days. In vivo observation period terminated 48-72 hours after last administration of Sorafenib and U4-3 as single therapy agent or in co-administration.

Figure 1:
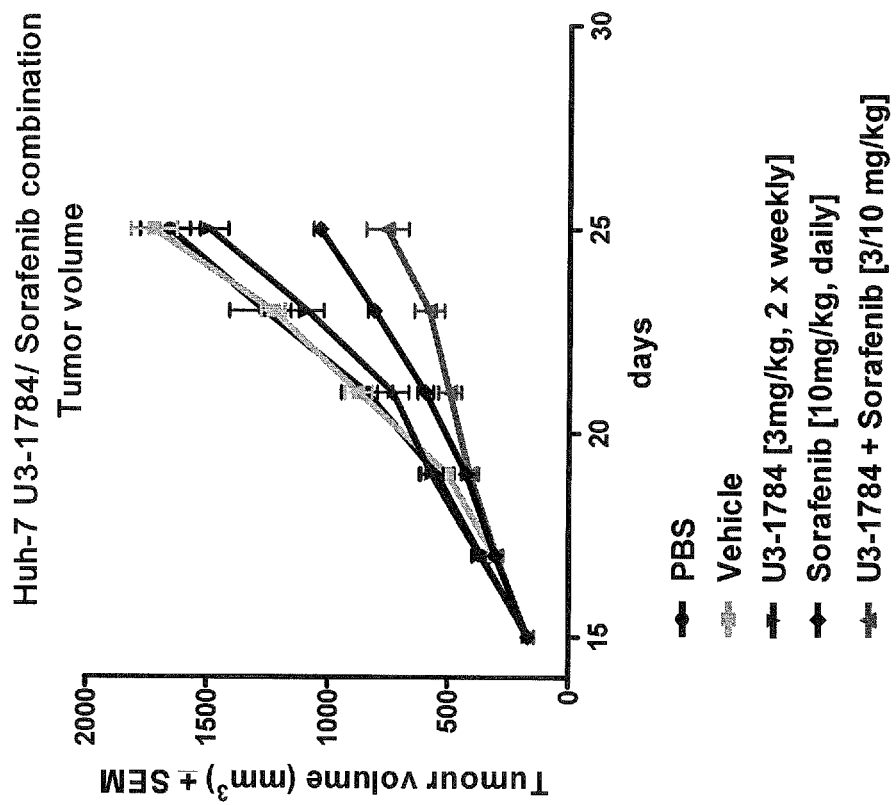
FIG. 1 shows the results of combination studies with Sorafenib and the antibody U4-3 in the treatment of hepatocellular carcinoma (HCC).

Statistical Analysis of Data of FIG. 1A

| Analyzed item | Statistic analysis |
|---|---|
| U4-3 | 3 mg/kg |
| vs | |
| U4-3 + Sorafenib | 3/10 mg/kg |
| Unpaired t test | |
| P-value | <0.0001 |
| Are means sign. different? (P < 0.005) | Yes |
| One- or two-tailed p-value? | Two-tailed |
| Analyzed item | |
| Sorafenib | 10 mg/kg |
| vs | |
| U4-3 + Sorafenib | 3/10 mg/kg |

-continued

| | Statistic analysis |
|---|---|
| Unpaired t test | |
| P-value | <0.0079 |
| Are means sign. different? (P < 0.005) | Yes |
| One- or two-tailed p-value? | Two-tailed |

Figure 1B:
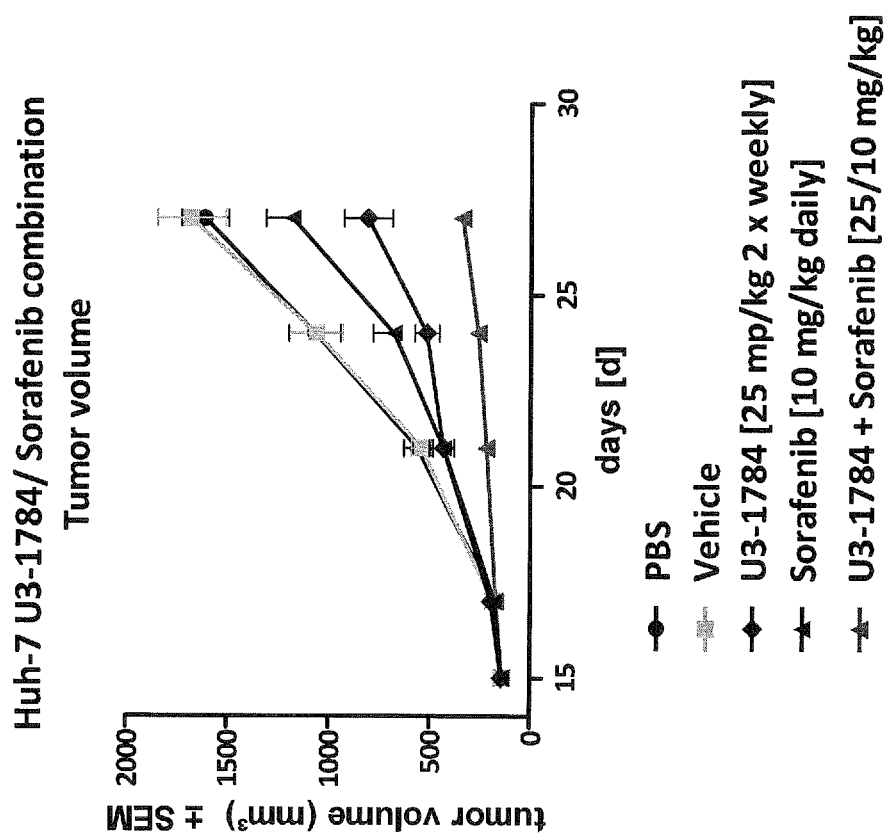
Figure 1:
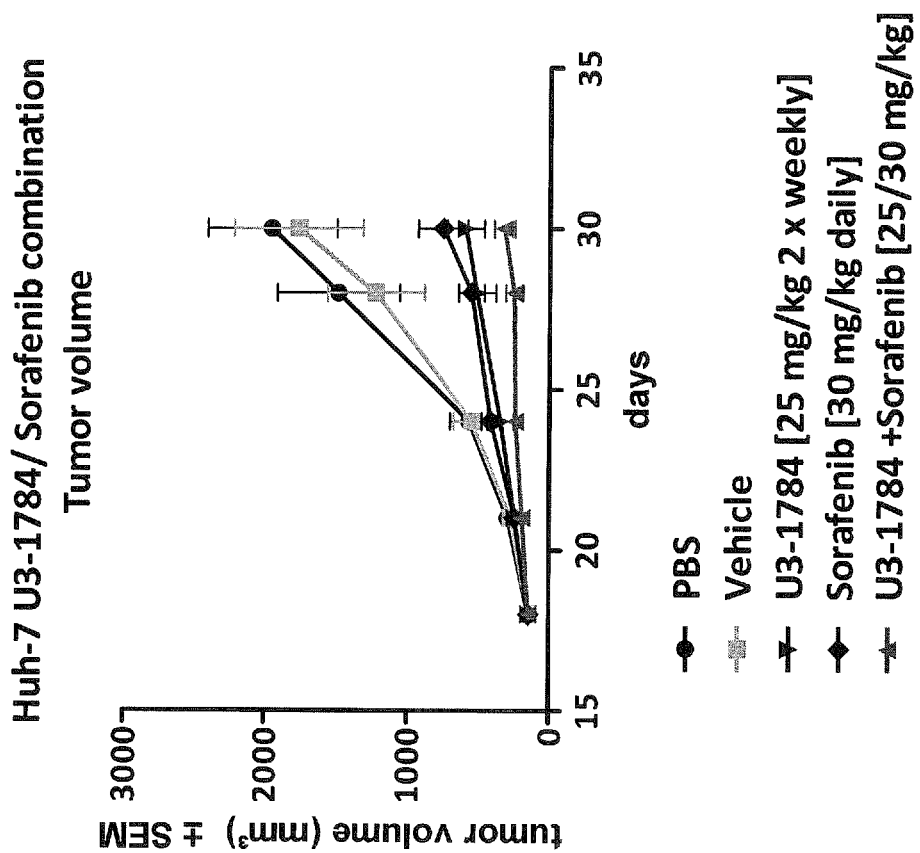
Figure 2:
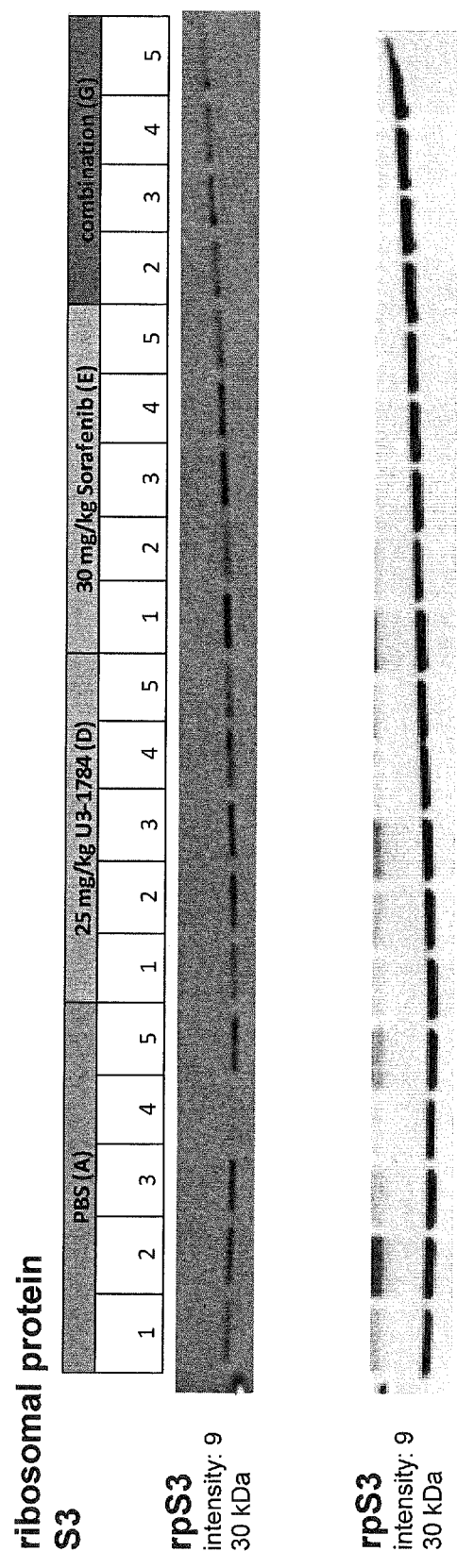
FIG. 2 shows a molecular analysis of the Huh-7 model.
Figure 2:
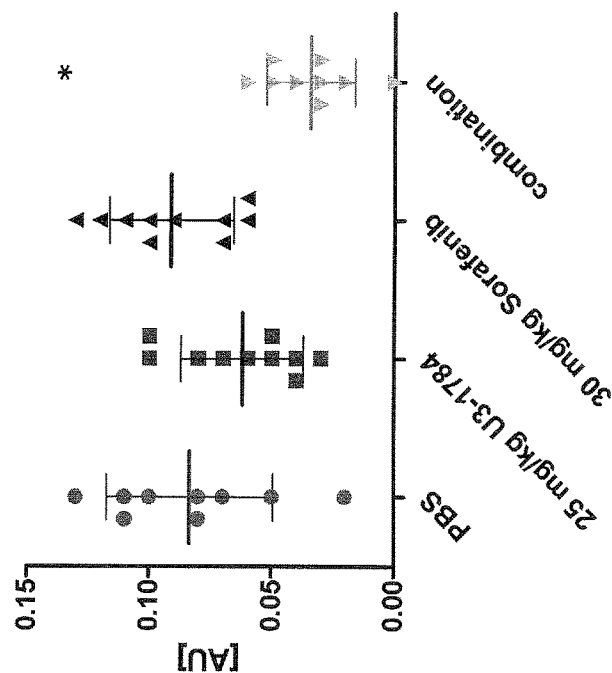

Statistical Analysis of Data of FIG. 1B

| Analyzed item | Statistic analysis |
|---|---|
| U4-3 | 25 mg/kg |
| vs | |
| U4-3 + Sorafenib | 25/10 mg/kg |
| Unpaired t test | |
| P-value | <0.0013 |
| Are means sign. different? (P < 0.005) | Yes |
| One- or two-tailed p-value? | Two-tailed |
| Analyzed item | |
| Sorafenib | 10 mg/kg |
| vs | |
| U4-3 + Sorafenib | 25/10 mg/kg |
| Unpaired t test | |
| P-value | <0.0001 |
| Are means sign. different? (P < 0.005) | Yes |
| One- or two-tailed p-value? | Two-tailed |

Statistical Analysis of Data of FIG. 1C

| Analyzed item | Statistic analysis |
|---|---|
| U4-3 | 25 mg/kg |
| vs | |
| U4-3 + Sorafenib | 25/30 mg/kg |
| Unpaired t test | |
| P-value | <0.0001 |
| Are means sign. different? (P <0.005) | Yes |
| One- or two-tailed p-value? | Two-tailed |
| Analyzed item | |
| Sorafenib | 30 mg/kg |
| vs | |
| U4-3 + Sorafenib | 25/30 mg/kg |
| Unpaired t test | |
| P-value | <0.0001 |
| Are means sign. different? (P < 0.005) | Yes |
| One- or two-tailed p-value? | Two-tailed |

Statistical analysis was done using the tumor volumes of the last measurement day, i.e. with 10 values in each group. An unpaired two-tailed t-test was performed with the indicated two groups using the GraphPad Prism Version 5.01. In order to show that the result with the combination treatment was significantly different from the single therapy treatments, it was considered that both t-tests which were performed for each in vivo study, had to yield P<0.05.

The present specification also includes an ASCII text file entitled "61474P-WO-replacement-seg-listing-FINAL-10-26-20.txt" that was created on Oct. 26, 2020, and has a file size of 42,661 bytes, the subject matter of which is incorporated by reference in its entirety.

The invention claimed is:

1. A method for the treatment of hepatocellular carcinoma (HCC), said method comprising administering an effective amount of a combination of (i) a human anti-FGFR4 antibody or an antigen-binding fragment of said antibody, and (ii) Sorafenib or a pharmaceutically acceptable salt thereof to a patient in need of such treatment, wherein the human anti-FGFR4 antibody or the antigen-binding fragment of said antibody is directed against an epitope between amino acids 119-248 of human FGFR4 (SEQ ID NO: 70), and comprises:
(i) a heavy chain comprising:
   (a) a CDRH1 as shown in SEQ ID NO: 3,
   (b) a CDRH2 as shown in SEQ ID NO: 8, and
   (c) a CDRH3 as shown in SEQ ID NO: 15,
and a light chain comprising:
   (d) a CDRL1 as shown in SEQ ID NO: 23,
   (e) a CDRL2 as shown in SEQ ID NO: 25, and
   (f) a CDRL3 as shown in SEQ ID NO: 30;
or
(ii) a heavy chain comprising:
   (a) a CDRH1 as shown in SEQ ID NO: 3,
   (b) a CDRH2 as shown in SEQ ID NO: 8, and
   (c) a CDRH3 as shown in SEQ ID NO: 15,
and a light chain comprising:
   (d) a CDRL1 as shown in SEQ ID NO: 68,
   (e) a CDRL2 as shown in SEQ ID NO: 27, and
   (f) a CDRL3 as shown in SEQ ID NO: 35.

2. The method of claim 1, wherein the human anti-FGFR4 antibody or the antigen-binding fragment of said antibody is a Fab fragment, a Fab' fragment, a F(ab'), fragment, a Fv fragment, a diabody, or a single chain antibody molecule.

3. The method of claim 1, wherein the human anti-FGFR4 antibody or the antigen-binding fragment of said antibody is of the IgG1-, IgG2-, IgG3- or IgG4-type.

4. The method of claim 1, said method further comprising chemotherapy or radiation.

5. The method of claim 1, wherein the human anti-FGFR4 antibody or the antigen-binding fragment of said antibody is coupled to a labeling group or to an effector group.

6. The method of claim 1, wherein the human anti-FGFR4 antibody or the antigen-binding fragment of said antibody is fused to IL-2.

7. A method for the treatment of hepatocellular carcinoma (HCC), said method comprising administering an effective amount of a combination of (i) a human anti-FGFR4 antibody or an antigen-binding fragment of said antibody, and (ii) Sorafenib or a pharmaceutically acceptable salt thereof to a patient in need of such treatment, wherein the human anti-FGFR4 antibody or the antigen-binding fragment of said antibody is directed against an epitope between amino acids 119-248 of human FGFR4 (SEQ ID NO: 70), and comprises:
a heavy chain comprising:
   (a) a CDRH1 as shown in SEQ ID NO: 3,
   (b) a CDRH2 as shown in SEQ ID NO: 8, and
   (c) a CDRH3 as shown in SEQ ID NO: 15,
and a light chain comprising:
   (d) a CDRL1 as shown in SEQ ID NO: 23,
   (e) a CDRL2 as shown in SEQ ID NO: 25, and
   (f) a CDRL3 as shown in SEQ ID NO: 30.

8. A method for the treatment of hepatocellular carcinoma (HCC), said method comprising administering an effective amount of a combination of (i) a human anti-FGFR4 antibody or an antigen-binding fragment of said antibody, and (ii) Sorafenib or a pharmaceutically acceptable salt thereof to a patient in need of such treatment, wherein the human anti-FGFR4 antibody or the antigen-binding fragment of said antibody is directed against an epitope between amino acids 119-248 of human FGFR4 (SEQ ID NO: 70), and comprises:
a heavy chain comprising:
(a) a CDRH1 as shown in SEQ ID NO: 3,
(b) a CDRH2 as shown in SEQ ID NO: 8, and
(c) a CDRH3 as shown in SEQ ID NO: 15,
and a light chain comprising:
(d) a CDRL1 as shown in SEQ ID NO: 68,
(e) a CDRL2 as shown in SEQ ID NO: 27, and
(f) a CDRL3 as shown in SEQ ID NO: 35.

* * * * *

SEQUENCE LISTING

<160> NUMBER OF SEQ ID NOS: 70

<210> SEQ ID NO 1
<211> LENGTH: 5
<212> TYPE: PRT
<213> ORGANISM: Artificial Sequence
<220> FEATURE:
<223> OTHER INFORMATION: U4-1-VH CDRH1

<400> SEQUENCE: 1

Arg Asn Tyr Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: U4-2-VH CDRH1

<400> SEQUENCE: 2

Lys Ala Trp Met Ser
1               5

<210> SEQ ID NO 3
<211> LENGTH: 5
<212> TYPE: PRT
<213> ORGANISM: Artificial Sequence
<220> FEATURE:
<223> OTHER INFORMATION: U4-3-VH, U4-7-VH and U4-9-VH CDRH1

<400> SEQUENCE: 3

Asp Tyr Tyr Met Ser
1               5

<210> SEQ ID NO 4
<211> LENGTH: 5
<212> TYPE: PRT
<213> ORGANISM: Artificial Sequence
<220> FEATURE:
<223> OTHER INFORMATION: U4-4-VH and U4-8-VH CDRH1

<400> SEQUENCE: 4

Ser Asn Tyr Met Ser
1               5

<210> SEQ ID NO 5
<211> LENGTH: 5
<212> TYPE: PRT
<213> ORGANISM: Artificial Sequence
<220> FEATURE:
<223> OTHER INFORMATION: U4-5-VH CDRH1

<400> SEQUENCE: 5

Ser Asn Tyr Met Asn
1               5

<210> SEQ ID NO 6
<211> LENGTH: 5
<212> TYPE: PRT
<213> ORGANISM: Artificial Sequence
<220> FEATURE:
<223> OTHER INFORMATION: U4-6-VH CDRH1

<400> SEQUENCE: 6

Asp Tyr Tyr Met Asn
1               5

```
<210> SEQ ID NO 7
<211> LENGTH: 17
<212> TYPE: PRT
<213> ORGANISM: Artificial Sequence
<220> FEATURE:
<223> OTHER INFORMATION: U4-1-VH, U4-2-VH and U4-7-VH CDRH2

<400> SEQUENCE: 7

Ala Ile Ser Gly Ser Gly Gly Ser Thr Tyr Tyr Ala Asp Ser Val Lys
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: U4-3-VH and U4-9-VH CDRH2

<400> SEQUENCE: 8

Thr Ile Ser Gly Ser Gly Gly Ser Thr Tyr Tyr Ala Asp Ser Val Lys
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: U4-4-VH CDRH2

<400> SEQUENCE: 9

Leu Ile Ser Gly Ser Gly Gly Ser Thr Tyr Tyr Ala Asp Ser Val Gln
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: U4-5-VH CDRH2

<400> SEQUENCE: 10

Val Ile Ser Tyr Asp Gly Ser Asn Lys Tyr Tyr Ala Asp Ser Val Lys
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: U4-8-VH CDRH2

<400> SEQUENCE: 11

Ser Ile Ser Gly Ser Gly Gly Arg Thr Tyr Tyr Ala Asp Ser Val Lys
1               5                   10                  15

Gly

<210> SEQ ID NO 12
<211> LENGTH: 17
```

```
<212> TYPE: PRT
<213> ORGANISM: Artificial Sequence
<220> FEATURE:
<223> OTHER INFORMATION: U4-6-VH CDRH2

<400> SEQUENCE: 12

Ala Ile Gly Gly Ser Gly Asp Arg Thr Tyr Tyr Ala Asp Ser Val Lys
1               5                   10                  15

Gly

<210> SEQ ID NO 13
<211> LENGTH: 9
<212> TYPE: PRT
<213> ORGANISM: Artificial Sequence
<220> FEATURE:
<223> OTHER INFORMATION: U4-1-VH CDRH3

<400> SEQUENCE: 13

Val Thr Ser Pro Gly Ala Phe Asp Ile
1               5

<210> SEQ ID NO 14
<211> LENGTH: 9
<212> TYPE: PRT
<213> ORGANISM: Artificial Sequence
<220> FEATURE:
<223> OTHER INFORMATION: U4-2-VH CDRH3

<400> SEQUENCE: 14

Leu Tyr Ser Tyr Gly Asp Phe Asp His
1               5

<210> SEQ ID NO 15
<211> LENGTH: 9
<212> TYPE: PRT
<213> ORGANISM: Artificial Sequence
<220> FEATURE:
<223> OTHER INFORMATION: U4-3-VH and U4-9-VH CDRH3

<400> SEQUENCE: 15

Leu Thr Ala Tyr Gly His Val Asp Ser
1               5

<210> SEQ ID NO 16
<211> LENGTH: 10
<212> TYPE: PRT
<213> ORGANISM: Artificial Sequence
<220> FEATURE:
<223> OTHER INFORMATION: U4-4-VH CDRH3

<400> SEQUENCE: 16

Asn Thr Ala Gly Phe Gly Tyr Phe Asp Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: U4-5-VH CDRH3

<400> SEQUENCE: 17

Lys Ser Arg Asp Phe Trp Arg Gly Pro Phe Asp Tyr
1               5                   10

<210> SEQ ID NO 18
```

```
<211> LENGTH: 9
<212> TYPE: PRT
<213> ORGANISM: Artificial Sequence
<220> FEATURE:
<223> OTHER INFORMATION: U4-8-VH CDRH3

<400> SEQUENCE: 18

Met Thr Val Phe Gly Ala Ala Thr Leu
1               5

<210> SEQ ID NO 19
<211> LENGTH: 7
<212> TYPE: PRT
<213> ORGANISM: Artificial Sequence
<220> FEATURE:
<223> OTHER INFORMATION: U4-6-VH CDRH3

<400> SEQUENCE: 19

Gly Gly Ser Tyr Phe Gly Tyr
1               5

<210> SEQ ID NO 20
<211> LENGTH: 9
<212> TYPE: PRT
<213> ORGANISM: Artificial Sequence
<220> FEATURE:
<223> OTHER INFORMATION: U4-7-VH CDRH3

<400> SEQUENCE: 20

Leu Ala Thr Tyr Gly Pro Phe Asp Asp
1               5

<210> SEQ ID NO 21
<211> LENGTH: 13
<212> TYPE: PRT
<213> ORGANISM: Artificial Sequence
<220> FEATURE:
<223> OTHER INFORMATION: U4-1-VL CDRL1

<400> SEQUENCE: 21

Ser Gly Gly Thr Ser Asn Ile Gly Thr Asn Thr Val Asn
1               5                   10

<210> SEQ ID NO 22
<211> LENGTH: 13
<212> TYPE: PRT
<213> ORGANISM: Artificial Sequence
<220> FEATURE:
<223> OTHER INFORMATION: U4-2-VL, U4-4-VL, U4-5-VL, U4-6-VL and U4-8-VL
      CDRL1

<400> SEQUENCE: 22

Ser Gly Ser Ser Ser Asn Ile Gly Ser Asn Thr Val Asn
1               5                   10

<210> SEQ ID NO 23
<211> LENGTH: 13
<212> TYPE: PRT
<213> ORGANISM: Artificial Sequence
<220> FEATURE:
<223> OTHER INFORMATION: U4-3-VL CDRL1

<400> SEQUENCE: 23

Ser Gly Ser Ser Ser Asn Ile Gly Thr Asn Thr Val Asn
1               5                   10

<210> SEQ ID NO 24
```

-continued

<210> SEQ ID NO 24
<211> LENGTH: 7
<212> TYPE: PRT
<213> ORGANISM: Artificial Sequence
<220> FEATURE:
<223> OTHER INFORMATION: U4-1-VL, U4-2-VL, U4-4-VL, U4-5-VL and U4-8-VL
      CDRL2

<400> SEQUENCE: 24

Arg Asn Asn Gln Arg Pro Ser
1               5

<210> SEQ ID NO 25
<211> LENGTH: 7
<212> TYPE: PRT
<213> ORGANISM: Artificial Sequence
<220> FEATURE:
<223> OTHER INFORMATION: U4-3-VL CDRL2

<400> SEQUENCE: 25

Arg Asn Tyr Gln Arg Pro Ser
1               5

<210> SEQ ID NO 26
<211> LENGTH: 7
<212> TYPE: PRT
<213> ORGANISM: Artificial Sequence
<220> FEATURE:
<223> OTHER INFORMATION: U4-6-VL CDRL2

<400> SEQUENCE: 26

Tyr Asp Asp Leu Leu Pro Ser
1               5

<210> SEQ ID NO 27
<211> LENGTH: 7
<212> TYPE: PRT
<213> ORGANISM: Artificial Sequence
<220> FEATURE:
<223> OTHER INFORMATION: U4-7-VL and U4-9-VL CDRL2

<400> SEQUENCE: 27

Arg Asn Asn Arg Arg Pro Ser
1               5

<210> SEQ ID NO 28
<211> LENGTH: 13
<212> TYPE: PRT
<213> ORGANISM: Artificial Sequence
<220> FEATURE:
<223> OTHER INFORMATION: U4-1-VL CDRL3

<400> SEQUENCE: 28

Ala Ala Trp Asp Asp Ser Leu Asn Gly Pro Tyr Val Val
1               5                   10

<210> SEQ ID NO 29
<211> LENGTH: 13
<212> TYPE: PRT
<213> ORGANISM: Artificial Sequence
<220> FEATURE:
<223> OTHER INFORMATION: U4-2-VL CDRL3

<400> SEQUENCE: 29

Ala Ala Trp Asp Asp Ser Leu Asn Gly Pro Ala Val Val
1               5                   10

<210> SEQ ID NO 30

```
<211> LENGTH: 13
<212> TYPE: PRT
<213> ORGANISM: Artificial Sequence
<220> FEATURE:
<223> OTHER INFORMATION: U4-3-VL CDRL3

<400> SEQUENCE: 30

Ala Ala Trp Asp Asp Ser Leu Ser Gly Pro His Val Val
1               5                   10

<210> SEQ ID NO 31
<211> LENGTH: 13
<212> TYPE: PRT
<213> ORGANISM: Artificial Sequence
<220> FEATURE:
<223> OTHER INFORMATION: U4-4-VL CDRL3

<400> SEQUENCE: 31

Ala Ala Trp Asp Asp Ser Leu Asn Gly Pro Leu Val Val
1               5                   10

<210> SEQ ID NO 32
<211> LENGTH: 11
<212> TYPE: PRT
<213> ORGANISM: Artificial Sequence
<220> FEATURE:
<223> OTHER INFORMATION: U4-5-VL CDRL3

<400> SEQUENCE: 32

Ser Thr Trp Asp Asp Ser Leu Arg Gly Trp Val
1               5                   10

<210> SEQ ID NO 33
<211> LENGTH: 13
<212> TYPE: PRT
<213> ORGANISM: Artificial Sequence
<220> FEATURE:
<223> OTHER INFORMATION: U4-8-VL CDRL3

<400> SEQUENCE: 33

Ala Ala Trp Asp Asp Ser Leu Asn Gly Pro Tyr Trp Val
1               5                   10

<210> SEQ ID NO 34
<211> LENGTH: 11
<212> TYPE: PRT
<213> ORGANISM: Artificial Sequence
<220> FEATURE:
<223> OTHER INFORMATION: U4-6-VL CDRL3

<400> SEQUENCE: 34

Ala Ala Trp Asp Asp Ser Leu Asn Gly Pro Val
1               5                   10

<210> SEQ ID NO 35
<211> LENGTH: 13
<212> TYPE: PRT
<213> ORGANISM: Artificial Sequence
<220> FEATURE:
<223> OTHER INFORMATION: U4-7-VL and U4-9-VL CDRL3

<400> SEQUENCE: 35

Ala Ala Trp Asp Asp Ser Leu Ser Gly Pro Asn Val Val
1               5                   10

<210> SEQ ID NO 36
<211> LENGTH: 354
```

```
<212> TYPE: DNA
<213> ORGANISM: Artificial Sequence
<220> FEATURE:
<223> OTHER INFORMATION: U4-1-VH

<400> SEQUENCE: 36
gaggtgcagc tgttggagtc tgggggaggc ttggtacagc ctggggggtc cctgagactc    60
tcctgtgcag cctctggatt caccttcagt agaaactaca tgagttgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac actgccgtgt attactgtgc gagagttacc   300
tcaccagggg cttttgatat ctggggccaa ggtaccctgg tcaccgtgag ctca          354

<210> SEQ ID NO 37
<211> LENGTH: 399
<212> TYPE: DNA
<213> ORGANISM: Artificial Sequence
<220> FEATURE:
<223> OTHER INFORMATION: U4-2-VH

<400> SEQUENCE: 37
gaggtgcagc tgttggagtc tgggggaggc ttggtacagc ctggggggtc cctgagactc    60
tcctgtgcag cctctggatt caccttcagt aaagcctgga tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac actgccgtgt attactgtgc gagattatac   300
agctatggtg actttgacca ctggggccaa ggtaccctgg tcaccgtgag ctcagcctcc   360
accaagggcc caagcgtctt ccccctggca ccctcctcc                          399

<210> SEQ ID NO 38
<211> LENGTH: 399
<212> TYPE: DNA
<213> ORGANISM: Artificial Sequence
<220> FEATURE:
<223> OTHER INFORMATION: U4-3-VH and U4-9-VH

<400> SEQUENCE: 38
gaggtgcagc tgttggagtc tgggggaggc ttggtacagc ctggggggtc cctgagactc    60
tcctgtgcag cctctggatt caccttcagt gactactaca tgagctggat ccgccaggct   120
ccagggaagg ggctggagtg ggtctcaact attagtggta gtggtggtag tacatactac   180
gcagactccg tgaagggccg gttcaccatc tccagagaca attccaagaa cacgctgtat   240
ctgcaaatga acagcctgag agccgaggac actgccgtgt attactgtgc cagactcacc   300
gcctatggcc acgtagactc ctggggccaa ggtaccctgg tcaccgtgag ctcagcctcc   360
accaagggcc caagcgtctt ccccctggca ccctcctcc                          399

<210> SEQ ID NO 39
<211> LENGTH: 402
<212> TYPE: DNA
<213> ORGANISM: Artificial Sequence
<220> FEATURE:
<223> OTHER INFORMATION: U4-4-VH

<400> SEQUENCE: 39
gaggtgcagc tgttggagtc tgggggaggc ttggtacagc ctggggggtc cctgagactc    60
```

| | |
|---|---|
| tcctgtgcag cctctggatt caccttcagt agcaactaca tgagctgggt ccgccaggct | 120 |
| ccagggaagg ggctggagtg ggtctcactt attagtggta gtggtggtag cacatactac | 180 |
| gcagactccg tgcagggccg cttcaccatc tccagagaca attccaagaa cacgctgtat | 240 |
| ctgcaaatga acagcctgag agccgaggac actgccgtgt attactgtgc gagaaatacg | 300 |
| gctggttttg ggtacttcga tctctggggc caaggtaccc tggtcaccgt gagctcagcc | 360 |
| tccaccaagg gcccaagcgt cttccccctg gcaccctcct cc | 402 |

```
<210> SEQ ID NO 40
<211> LENGTH: 408
<212> TYPE: DNA
<213> ORGANISM: Artificial Sequence
<220> FEATURE:
<223> OTHER INFORMATION: U4-5-VH

<400> SEQUENCE: 40
```

| | |
|---|---|
| gaggtgcagc tgttggagtc tgggggaggc ttggtacagc ctgggggtc cctgagactc | 60 |
| tcctgtgcag cctctggatt caccttcagt agcaactaca tgaactgggt ccgccaggct | 120 |
| ccagggaagg ggctggagtg ggtggcagtt atatcatatg atggaagtaa taaatactac | 180 |
| gcagactccg tgaagggccg attcaccatc tccagagaca attccaagaa cacgctgtat | 240 |
| ctgcaaatga acagcctgag agccgaggac actgccgtgt attactgtgt gacaaagtct | 300 |
| cgagattttt ggcggggtcc ctttgactac tggggccaag gtaccctggt caccgtgagc | 360 |
| tcagcctcca ccaagggccc aagcgtcttc cccctggcac cctcctcc | 408 |

```
<210> SEQ ID NO 41
<211> LENGTH: 399
<212> TYPE: DNA
<213> ORGANISM: Artificial Sequence
<220> FEATURE:
<223> OTHER INFORMATION: U4-8-VH

<400> SEQUENCE: 41
```

| | |
|---|---|
| gaggtgcagc tgttggagtc tgggggaggc ttggtacagc ctgggggtc cctgagactc | 60 |
| tcctgtgcag cctctggatt caccttcagt agcaactaca tgagctgggt ccgccaggct | 120 |
| ccagggaagg ggctggagtg ggtctcaagt attagtggta gtggtggtcg cacatactac | 180 |
| gcagactccg tgaagggccg attcaccatc tccagagaca attccaagaa cacgctgtat | 240 |
| ctgcaaatga acagcctgag agccgaggac actgccgtgt attactgtgc gagaatgacg | 300 |
| gtctttggag cggcaacgct ctggggccaa ggtaccctgg tcaccgtgag ctcagcctcc | 360 |
| accaagggcc caagcgtctt ccccctggca ccctcctcc | 399 |

```
<210> SEQ ID NO 42
<211> LENGTH: 393
<212> TYPE: DNA
<213> ORGANISM: Artificial Sequence
<220> FEATURE:
<223> OTHER INFORMATION: U4-6-VH

<400> SEQUENCE: 42
```

| | |
|---|---|
| gaggtgcagc tgttggagtc tgggggaggc ttggtacagc ctgggggtc cctgagactc | 60 |
| tcctgtgcag cctctggatt caccttcagt gactactaca tgaactgggt ccgccaggct | 120 |
| ccaggcaagg ggctggagtg ggtctcagct attggtggta gtggtgatag aacatactac | 180 |
| gcagactccg tgaagggccg gttcaccatc tccagagaca attccaagaa cacgctgtat | 240 |
| ctgcaaatga acagcctgag agccgaggac actgccgtgt attactgtgc tctcggtggg | 300 |

```
agctacttcg gctactgggg ccaaggtacc ctggtcaccg tgagctcagc ctccaccaag    360
ggcccaagcg tcttccccct ggcaccctcc tcc                                 393

<210> SEQ ID NO 43
<211> LENGTH: 399
<212> TYPE: DNA
<213> ORGANISM: Artificial Sequence
<220> FEATURE:
<223> OTHER INFORMATION: U4-7-VH

<400> SEQUENCE: 43
gaggtgcagc tgttggagtc tgggggaggc ttggtacagc ctgggggtc cctgagactc      60 tcctgtgcag cctctggatt caccttcagt gactactaca tgagctgggt ccgccaggct    120
cccgggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac actgccgtgt attactgtgc gaccctggcc    300
acctacggac catttgacga ctggggccaa ggtaccctgg tcaccgtgag ctcagcctcc    360
accaagggcc caagcgtctt ccccctggca ccctcctcc                           399

<210> SEQ ID NO 44
<211> LENGTH: 345
<212> TYPE: DNA
<213> ORGANISM: Artificial Sequence
<220> FEATURE:
<223> OTHER INFORMATION: U4-1-VL

<400> SEQUENCE: 44
cagtctgtgc tgactcagcc accctcagcg tctgggaccc ccgggcagag ggtcaccatc     60
tcttgttctg gaggcacctc caacatcgga actaatactg taaactggta tcagcagctc    120
ccaggaacgg cccccaaact cctcatctat aggaataatc agcggccctc agggggtccct   180 gaccgattct ctggctccaa gtctggcacc tcatcctccc tggccatcag tgggctccgg    240
tccgaggatg aggctgatta ttactgtgca gcatgggatg acagcctgaa tggtccctat    300
gtggtattcg gcggaggaac caagctgacg gtcctaggtc agcct                    345

<210> SEQ ID NO 45
<211> LENGTH: 345
<212> TYPE: DNA
<213> ORGANISM: Artificial Sequence
<220> FEATURE:
<223> OTHER INFORMATION: U4-2-VL

<400> SEQUENCE: 45
cagtctgtgc tgactcagcc accctcagcg tctgggaccc ccgggcagag ggtcaccatc     60
tcttgttctg gaagcagctc caacatcgga agtaatactg taaactggta tcagcagctc    120
ccaggaacgg cccccaaact cctcatctat cggaataatc agcggccctc agggggtccct   180 gaccgattct ctggctccaa gtctggcacc tcagcctccc tggccatcag tgggctccgg    240
tccgaggatg aggctgatta ttactgtgca gcatgggatg acagcctgaa tggtcccgct    300
gtggtattcg gcggaggaac caagctgacg gtcctaggtc agcct                    345

<210> SEQ ID NO 46
<211> LENGTH: 345
<212> TYPE: DNA
<213> ORGANISM: Artificial Sequence
<220> FEATURE:
```

<223> OTHER INFORMATION: U4-3-VL

<400> SEQUENCE: 46

| cagtctgtgc | tgactcagcc | accctcagcg | tctgggaccc | ccgggcagag | ggtcaccatc | 60 |
| tcttgttctg | gaagcagctc | caacatcgga | actaatactg | tgaactggta | tcagcagctc | 120 |
| ccaggaacgg | cccccaaact | cctcatctat | aggaattatc | agagaccctc | aggggtccct | 180 |
| gaccgattct | ctggctccaa | gtctggcacc | tcagcctccc | tggccatcag | tgggctccgg | 240 |
| tccgaggatg | aggctgatta | ttactgtgca | gcatgggatg | atagcctgag | tggtccacat | 300 |
| gtggtattcg | gcggaggaac | caagctgacg | gtcctaggtc | agcct | | 345 |

<210> SEQ ID NO 47
<211> LENGTH: 345
<212> TYPE: DNA
<213> ORGANISM: Artificial Sequence
<220> FEATURE:
<223> OTHER INFORMATION: U4-4-VL

<400> SEQUENCE: 47

| cagtctgtgc | tgactcagcc | accctcagcg | tctgggaccc | ccgggcagag | ggtcaccatc | 60 |
| tcttgttctg | gaagcagctc | caacatcgga | agtaatactg | taaactggta | tcagcagctc | 120 |
| ccaggaacgg | cccccaaact | cctcatctat | aggaataatc | agcggccctc | aggggtccct | 180 |
| gaccgattct | ctggctccaa | gtctggcacc | tcagcctccc | tggccatcag | tgggctccgg | 240 |
| tccgaggatg | aggctgatta | ttactgtgca | gcatgggatg | acagcctgaa | tggtccccta | 300 |
| gtggtattcg | gcggaggaac | caagctgacg | gtcctaggtc | agcct | | 345 |

<210> SEQ ID NO 48
<211> LENGTH: 339
<212> TYPE: DNA
<213> ORGANISM: Artificial Sequence
<220> FEATURE:
<223> OTHER INFORMATION: U4-5-VL

<400> SEQUENCE: 48

| cagtctgtgc | tgactcagcc | accctcagcg | tctgggaccc | ccgggcagag | ggtcaccatc | 60 |
| tcttgttctg | gaagcagctc | caacatcgga | agtaatactg | taaactggta | tcagcagctc | 120 |
| ccaggaacgg | cccccaaact | cctcatctat | aggaataatc | agcggccctc | aggggtccct | 180 |
| gaccgattct | ctggctccaa | gtctggcacc | tcagcctccc | tggccatcag | tgggctccgg | 240 |
| tccgaggatg | aggctgatta | ttactgttca | acgtgggatg | acagcctgag | aggttgggtg | 300 |
| ttcggcggag | gaaccaagct | gacggtccta | ggtcagcct | | | 339 |

<210> SEQ ID NO 49
<211> LENGTH: 345
<212> TYPE: DNA
<213> ORGANISM: Artificial Sequence
<220> FEATURE:
<223> OTHER INFORMATION: U4-8-VL

<400> SEQUENCE: 49

| cagtctgtgc | tgactcagcc | accctcagca | tctgggaccc | ccgggcagag | ggtcaccatc | 60 |
| tcttgttctg | gaagcagctc | caacatcgga | agtaatactg | taaactggta | tcagcagctc | 120 |
| ccaggaacgg | cccccaaact | cctcatctat | aggaataatc | agcggccctc | aggggtccct | 180 |
| gaccgattct | ctggctccaa | gtctggcacc | tcagcctccc | tggccatcag | tgggctccgg | 240 |
| tccgaggatg | aggctgatta | ttactgtgca | gcatgggatg | acagcctgaa | tggtccctat | 300 | tgggtgttcg gcggaggaac caagctgacg gtcctaggtc agcct        345

<210> SEQ ID NO 50
<211> LENGTH: 339
<212> TYPE: DNA
<213> ORGANISM: Artificial Sequence
<220> FEATURE:
<223> OTHER INFORMATION: U4-6-VL

<400> SEQUENCE: 50
cagtctgtgc tgactcagcc accctcagcg tctgggaccc ccgggcagag ggtcaccatc    60
tcttgttctg gaagcagctc caacatcgga agtaatactg taaactggta tcagcagctc   120
ccaggaacgg cccccaaact cctcatctat tatgatgatc tgctgccctc aggggtccct   180
gaccgattct ctggctccaa gtctggcacc tcagcctccc tggccatcag tgggctccgg   240
tccgaggatg aggctgatta ttactgtgca gcatgggatg acagcctgaa tggtccggtg   300
ttcggcggag gaaccaagct gacggtccta ggtcagcct                          339

<210> SEQ ID NO 51
<211> LENGTH: 345
<212> TYPE: DNA
<213> ORGANISM: Artificial Sequence
<220> FEATURE:
<223> OTHER INFORMATION: U4-7-VL and U4-9-VL

<400> SEQUENCE: 51
cagtctgtgc tgactcagcc accctcagcg tctgggaccc ccgggcagag ggtcaccatc    60
tcttgttctg gaagcagctc caacatcgga agtaatactg tacactggta tcagcagctc   120
ccaggaacgg cccccaaact cctcatctat agaaataatc ggcggccctc aggggtccct   180
gaccgattct ctggctccaa gtctggcacc tcagcctccc tggccatcag tgggctccgg   240
tccgaggatg aggctgatta ttactgtgca gcatgggatg acagcctgag tggtccgaat   300
gtggtattcg gcggaggaac caagctgacg gtcctaggtc agcct                   345

<210> SEQ ID NO 52
<211> LENGTH: 118
<212> TYPE: PRT
<213> ORGANISM: Artificial Sequence
<220> FEATURE:
<223> OTHER INFORMATION: U4-1-VH

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Thr Ser Pro Gly Ala Phe Asp Ile Trp Gly Gln Gly Thr
            100                 105                 110

Leu Val Thr Val Ser Ser

115

<210> SEQ ID NO 53
<211> LENGTH: 133
<212> TYPE: PRT
<213> ORGANISM: Artificial Sequence
<220> FEATURE:
<223> OTHER INFORMATION: U4-2-VH

<400> SEQUENCE: 53

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Ala
            20                  25                  30

Trp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Ser Tyr Gly Asp Phe Asp His Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser
    130
```

<210> SEQ ID NO 54
<211> LENGTH: 133
<212> TYPE: PRT
<213> ORGANISM: Artificial Sequence
<220> FEATURE:
<223> OTHER INFORMATION: U4-3-VH and U4-9-VH

<400> SEQUENCE: 54

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Thr Ala Tyr Gly His Val Asp Ser Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser
    130
```

<210> SEQ ID NO 55
<211> LENGTH: 134

```
<212> TYPE: PRT
<213> ORGANISM: Artificial Sequence
<220> FEATURE:
<223> OTHER INFORMATION: U4-4-VH

<400> SEQUENCE: 55
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Leu Ile Ser Gly Ser Gly Ser Thr Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Thr Ala Gly Phe Gly Tyr Phe Asp Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser
        130

```
<210> SEQ ID NO 56
<211> LENGTH: 136
<212> TYPE: PRT
<213> ORGANISM: Artificial Sequence
<220> FEATURE:
<223> OTHER INFORMATION: U4-5-VH

<400> SEQUENCE: 56
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Asn Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Thr Lys Ser Arg Asp Phe Trp Arg Gly Pro Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser
        130                 135

```
<210> SEQ ID NO 57
<211> LENGTH: 133
<212> TYPE: PRT
<213> ORGANISM: Artificial Sequence
<220> FEATURE:
<223> OTHER INFORMATION: U4-8-VH
```

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Ser Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Thr Val Phe Gly Ala Ala Thr Leu Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser
        130

<210> SEQ ID NO 58
<211> LENGTH: 131
<212> TYPE: PRT
<213> ORGANISM: Artificial Sequence
<220> FEATURE:
<223> OTHER INFORMATION: U4-6-VH

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Val Arg Gln Ala Pro Gly Lys Gly Leu Glu Trp Val
        35                  40                  45

Ser Ala Ile Gly Gly Ser Gly Asp Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Gly Gly Ser Tyr Phe Gly Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser
    130

<210> SEQ ID NO 59
<211> LENGTH: 133
<212> TYPE: PRT
<213> ORGANISM: Artificial Sequence
<220> FEATURE:
<223> OTHER INFORMATION: U4-7-VH

<400> SEQUENCE: 59

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Thr Leu Ala Thr Tyr Gly Pro Phe Asp Asp Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser
    130
```

<210> SEQ ID NO 60
<211> LENGTH: 115
<212> TYPE: PRT
<213> ORGANISM: Artificial Sequence
<220> FEATURE:
<223> OTHER INFORMATION: U4-1-VL

<400> SEQUENCE: 60

```
Gln Ser Val Leu Thr Gln Pro Pro Ser Ala Ser Gly Thr Pro Gly Gln
 1               5                  10                  15

Arg Val Thr Ile Ser Cys Ser Gly Gly Thr Ser Asn Ile Gly Thr Asn
            20                  25                  30

Thr Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ser Leu Ala Ile Ser Gly Leu Arg
 65                  70                  75                  80

Ser Glu Asp Glu Ala Asp Tyr Tyr Cys Ala Ala Trp Asp Asp Ser Leu
                85                  90                  95

Asn Gly Pro Tyr Val Val Phe Gly Gly Gly Thr Lys Leu Thr Val Leu
            100                 105                 110

Gly Gln Pro
        115
```

<210> SEQ ID NO 61
<211> LENGTH: 115
<212> TYPE: PRT
<213> ORGANISM: Artificial Sequence
<220> FEATURE:
<223> OTHER INFORMATION: U4-2-VL

<400> SEQUENCE: 61

```
Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60
```

```
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Asn Gly Pro Ala Val Val Phe Gly Gly Gly Thr Lys Leu Thr Val Leu
            100                 105                 110

Gly Gln Pro
        115

<210> SEQ ID NO 62
<211> LENGTH: 115
<212> TYPE: PRT
<213> ORGANISM: Artificial Sequence
<220> FEATURE:
<223> OTHER INFORMATION: U4-3-VL

<400> SEQUENCE: 62

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Thr Asn
             20                  25                  30

Thr Val Asn Trp Tyr Gln Gln Leu Pro Gly Thr Ala Pro Lys Leu Leu
             35                  40                  45

Ile Tyr Arg Asn Tyr Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Pro His Val Val Phe Gly Gly Gly Thr Lys Leu Thr Val Leu
            100                 105                 110

Gly Gln Pro
        115

<210> SEQ ID NO 63
<211> LENGTH: 115
<212> TYPE: PRT
<213> ORGANISM: Artificial Sequence
<220> FEATURE:
<223> OTHER INFORMATION: U4-4-VL

<400> SEQUENCE: 63

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Asn Ile Gly Ser Asn
             20                  25                  30

Thr Val Asn Trp Tyr Gln Gln Leu Pro Gly Thr Ala Pro Lys Leu Leu
             35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Asn Gly Pro Leu Val Val Phe Gly Gly Gly Thr Lys Leu Thr Val Leu
            100                 105                 110

Gly Gln Pro
```

<210> SEQ ID NO 64
<211> LENGTH: 113
<212> TYPE: PRT
<213> ORGANISM: Artificial Sequence
<220> FEATURE:
<223> OTHER INFORMATION: U4-5-VL

<400> SEQUENCE: 64

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Thr Trp Asp Asp Ser Leu
                85                  90                  95

Arg Gly Trp Val Phe Gly Gly Gly Thr Lys Leu Thr Val Leu Gly Gln
            100                 105                 110

Pro
```

<210> SEQ ID NO 65
<211> LENGTH: 115
<212> TYPE: PRT
<213> ORGANISM: Artificial Sequence
<220> FEATURE:
<223> OTHER INFORMATION: U4-8-VL

<400> SEQUENCE: 65

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Pro Tyr Trp Val Phe Gly Gly Gly Thr Lys Leu Thr Val Leu
            100                 105                 110

Gly Gln Pro
        115
```

<210> SEQ ID NO 66
<211> LENGTH: 113
<212> TYPE: PRT
<213> ORGANISM: Artificial Sequence
<220> FEATURE:
<223> OTHER INFORMATION: U4-6-VL

<400> SEQUENCE: 66

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Tyr Asp Asp Leu Leu Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Gln
            100                 105                 110

Pro
```

<210> SEQ ID NO 67
<211> LENGTH: 115
<212> TYPE: PRT
<213> ORGANISM: Artificial Sequence
<220> FEATURE:
<223> OTHER INFORMATION: U4-7-VL and U4-9-VL

<400> SEQUENCE: 67

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val His Trp Tyr Gln Gln Leu Pro Gly Thr Ala Pro Lys Leu Leu
            35                  40                  45

Ile Tyr Arg Asn Asn Arg Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro Asn Val Val Phe Gly Gly Gly Thr Lys Leu Thr Val Leu
            100                 105                 110

Gly Gln Pro
        115
```

<210> SEQ ID NO 68
<211> LENGTH: 13
<212> TYPE: PRT
<213> ORGANISM: Artificial Sequence
<220> FEATURE:
<223> OTHER INFORMATION: U4-7 and U4-9 CDRL1

<400> SEQUENCE: 68

```
Ser Gly Ser Ser Ser Asn Ile Gly Ser Asn Thr Val His
1               5                   10
```

<210> SEQ ID NO 69
<211> LENGTH: 4
<212> TYPE: PRT
<213> ORGANISM: Artificial Sequence
<220> FEATURE:
<223> OTHER INFORMATION: epitope

<400> SEQUENCE: 69

Arg Tyr Asn Tyr
1

<210> SEQ ID NO 70
<211> LENGTH: 802
<212> TYPE: PRT
<213> ORGANISM: Artificial Sequence
<220> FEATURE:
<223> OTHER INFORMATION: FGFR4

<400> SEQUENCE: 70

```
Met Arg Leu Leu Leu Ala Leu Leu Gly Val Leu Leu Ser Val Pro Gly
                 5                  10                  15

Pro Pro Val Leu Ser Leu Glu Ala Ser Glu Glu Val Glu Leu Glu Pro
             20                  25                  30

Cys Leu Ala Pro Ser Leu Glu Gln Gln Glu Gln Glu Leu Thr Val Ala
         35                  40                  45

Leu Gly Gln Pro Val Arg Leu Cys Cys Gly Arg Ala Glu Arg Gly Gly
     50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                 85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Thr Pro Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350
```

```
Glu Glu Asp Pro Thr Trp Thr Ala Ala Ala Pro Glu Ala Arg Tyr Thr
        355                 360                 365
Asp Ile Ile Leu Tyr Ala Ser Gly Ser Leu Ala Leu Ala Val Leu Leu
    370                 375                 380
Leu Leu Ala Gly Leu Tyr Arg Gly Gln Ala Leu His Gly Arg His Pro
385                 390                 395                 400
Arg Pro Pro Ala Thr Val Gln Lys Leu Ser Arg Phe Pro Leu Ala Arg
                405                 410                 415
Gln Phe Ser Leu Glu Ser Gly Ser Ser Gly Lys Ser Ser Ser Ser Leu
            420                 425                 430
Val Arg Gly Val Arg Leu Ser Ser Ser Gly Pro Ala Leu Leu Ala Gly
        435                 440                 445
Leu Val Ser Leu Asp Leu Pro Leu Asp Pro Leu Trp Glu Phe Pro Arg
    450                 455                 460
Asp Arg Leu Val Leu Gly Lys Pro Leu Gly Glu Gly Cys Phe Gly Gln
465                 470                 475                 480
Val Val Arg Ala Glu Ala Phe Gly Met Asp Pro Ala Arg Pro Asp Gln
                485                 490                 495
Ala Ser Thr Val Ala Val Lys Met Leu Lys Asp Asn Ala Ser Asp Lys
            500                 505                 510
Asp Leu Ala Asp Leu Val Ser Glu Met Glu Val Met Lys Leu Ile Gly
        515                 520                 525
Arg His Lys Asn Ile Ile Asn Leu Leu Gly Val Cys Thr Gln Glu Gly
    530                 535                 540
Pro Leu Tyr Val Ile Val Glu Cys Ala Ala Lys Gly Asn Leu Arg Glu
545                 550                 555                 560
Phe Leu Arg Ala Arg Arg Pro Pro Gly Pro Asp Leu Ser Pro Asp Gly
                565                 570                 575
Pro Arg Ser Ser Glu Gly Pro Leu Ser Phe Pro Val Leu Val Ser Cys
            580                 585                 590
Ala Tyr Gln Val Ala Arg Gly Met Gln Tyr Leu Glu Ser Arg Lys Cys
        595                 600                 605
Ile His Arg Asp Leu Ala Ala Arg Asn Val Leu Val Thr Glu Asp Asn
    610                 615                 620
Val Met Lys Ile Ala Asp Phe Gly Leu Ala Arg Gly Val His His Ile
625                 630                 635                 640
Asp Tyr Tyr Lys Lys Thr Ser Asn Gly Arg Leu Pro Val Lys Trp Met
                645                 650                 655
Ala Pro Glu Ala Leu Phe Asp Arg Val Tyr Thr His Gln Ser Asp Val
            660                 665                 670
Trp Ser Phe Gly Ile Leu Leu Trp Glu Ile Phe Thr Leu Gly Gly Ser
        675                 680                 685
Pro Tyr Pro Gly Ile Pro Val Glu Glu Leu Phe Ser Leu Leu Arg Glu
    690                 695                 700
Gly His Arg Met Asp Arg Pro Pro His Cys Pro Glu Leu Tyr Gly
705                 710                 715                 720
Leu Met Arg Glu Cys Trp His Ala Ala Pro Ser Gln Arg Pro Thr Phe
                725                 730                 735
Lys Gln Leu Val Glu Ala Leu Asp Lys Val Leu Leu Ala Val Ser Glu
            740                 745                 750
Glu Tyr Leu Asp Leu Arg Leu Thr Phe Gly Pro Tyr Ser Pro Ser Gly
        755                 760                 765
```

```
                                        -continued
Gly Asp Ala Ser Ser Thr Cys Ser Ser Ser Asp Ser Val Phe Ser His
    770                 775             780

Asp Pro Leu Pro Leu Gly Ser Ser Ser Phe Pro Phe Gly Ser Gly Val
785                 790                 795                 800

Gln Thr
```